United States Patent
Wang

(10) Patent No.: US 11,951,298 B2
(45) Date of Patent: Apr. 9, 2024

(54) COIL WINDING PATTERN FOR ENHANCED MOTOR EFFICIENCY

(71) Applicant: ABIOMED, Inc., Danvers, MA (US)

(72) Inventor: Jimpo Wang, Danvers, MA (US)

(73) Assignee: ABIOMED, INC., Danvers, MA (US)

( * ) Notice: Subject to any disclaimer, the term of this patent is extended or adjusted under 35 U.S.C. 154(b) by 817 days.

(21) Appl. No.: 16/880,043

(22) Filed: May 21, 2020

(65) Prior Publication Data

US 2020/0376181 A1  Dec. 3, 2020

Related U.S. Application Data

(60) Provisional application No. 62/853,999, filed on May 29, 2019.

(51) Int. Cl.
*A61M 60/419* (2021.01)
*A61M 60/13* (2021.01)
(Continued)

(52) U.S. Cl.
CPC .......... *A61M 60/419* (2021.01); *A61M 60/13* (2021.01); *A61M 60/139* (2021.01);
(Continued)

(58) Field of Classification Search
CPC ........ A61M 1/10; A61M 1/12; A61M 60/419; A61M 1/1036; A61M 1/125; A61M 1/1046; A61M 1/1008
See application file for complete search history.

(56) References Cited

U.S. PATENT DOCUMENTS 5,294,855 A † 3/1994 Mihalko
7,011,620 B1 † 3/2006 Siess
(Continued)

FOREIGN PATENT DOCUMENTS

CN  107104570 A  8/2017
CN  107112834 A  8/2017
(Continued)

OTHER PUBLICATIONS

International Search Report and Written Opinion for Application No. PCT/US2020/033990 dated Aug. 5, 2020.
Office Action from corresponding Indian Patent Application No. 202117059150 dated Aug. 4, 2023 (6 pp.).

*Primary Examiner* — Matthew W Schall
(74) *Attorney, Agent, or Firm* — Botos Churchill IP Law LLP

(57) ABSTRACT

There is provided an intravascular blood pump for insertion into a patient's body. The system comprises a slotless motor having p magnet pole pairs and n phases, where p is an integer greater than zero, and n is an integer $\geq 3$. The motor comprises a stator winding having $2np$ coils wound to form two coils per phase per magnet pole pair such that a coil from each phase is circumferentially arranged next to a coil from a different phase in a sequential order of phase, the arrangement repeated along the stator winding such that each coil spans $360°/(2np)$ about the cross section of the stator winding. The motor also comprises a permanent magnet rotor supported for rotation and configured to generate a magnetic flux for interaction with the stator winding. The two coils per phase per magnet pole pair are connected in series.

24 Claims, 10 Drawing Sheets

(51) Int. Cl.
*A61M 60/139* (2021.01)
*A61M 60/165* (2021.01)
*A61M 60/216* (2021.01)
*A61M 60/416* (2021.01)
*A61M 60/857* (2021.01)
*H02K 1/278* (2022.01)

(52) U.S. Cl.
CPC ........ *A61M 60/165* (2021.01); *A61M 60/216* (2021.01); *A61M 60/416* (2021.01); *A61M 60/857* (2021.01); *H02K 1/278* (2013.01)

(56) References Cited

U.S. PATENT DOCUMENTS

| | | | |
|---|---|---|---|
| 8,829,756 B2 * | 9/2014 | Suzuki | H02K 15/0442 310/184 |
| 2014/0010686 A1 * | 1/2014 | Tanner | A61M 60/808 600/16 |
| 2016/0134165 A1 | 5/2016 | Luedi et al. | |

FOREIGN PATENT DOCUMENTS

| | | |
|---|---|---|
| EP | 2466731 A1 | 6/2012 |
| WO | 2018069203 A1 | 4/2018 |
| WO | 2018139245 A1 | 8/2018 |
| WO | 2019057636 A1 | 3/2019 |

\* cited by examiner
† cited by third party

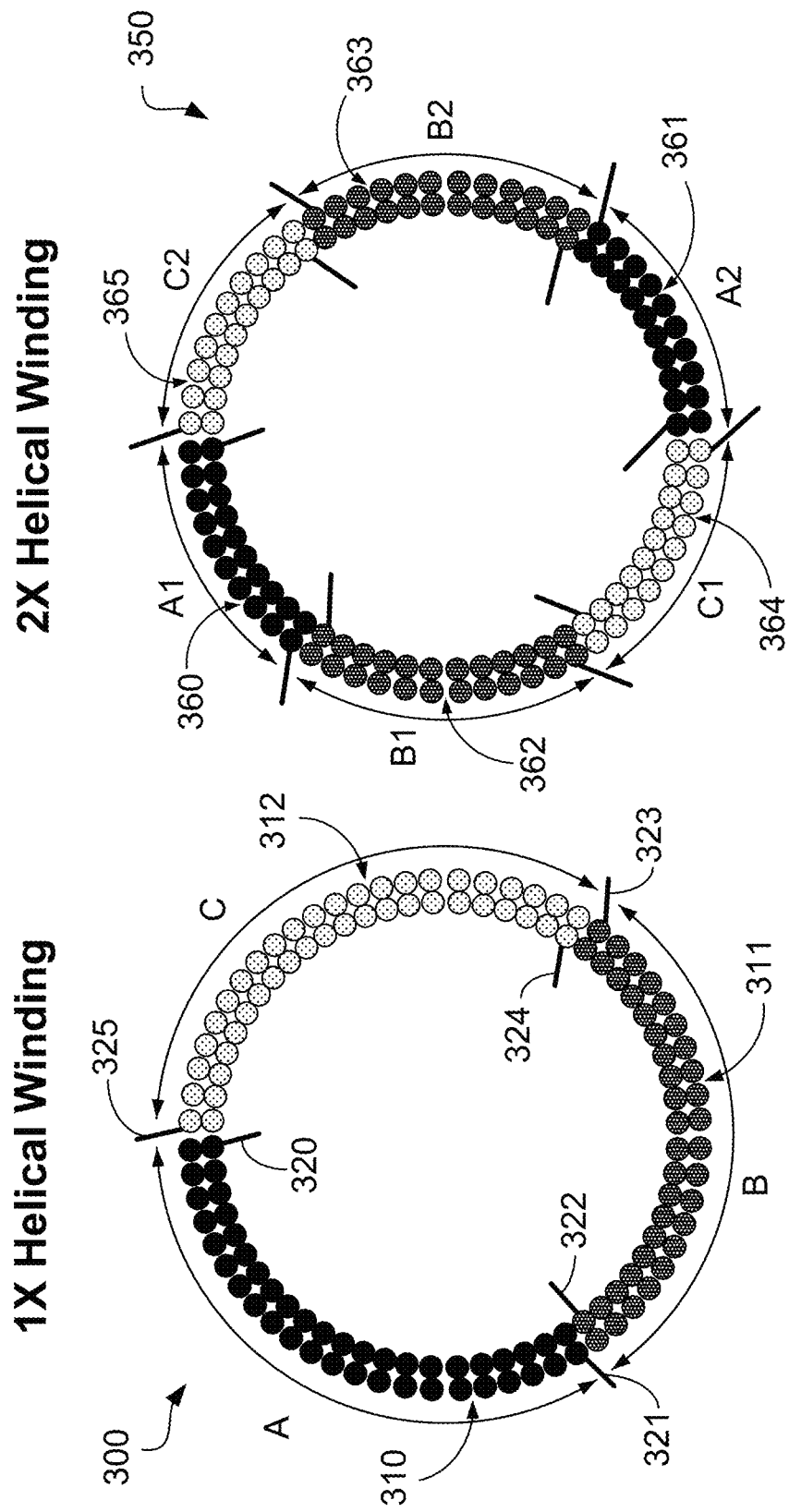

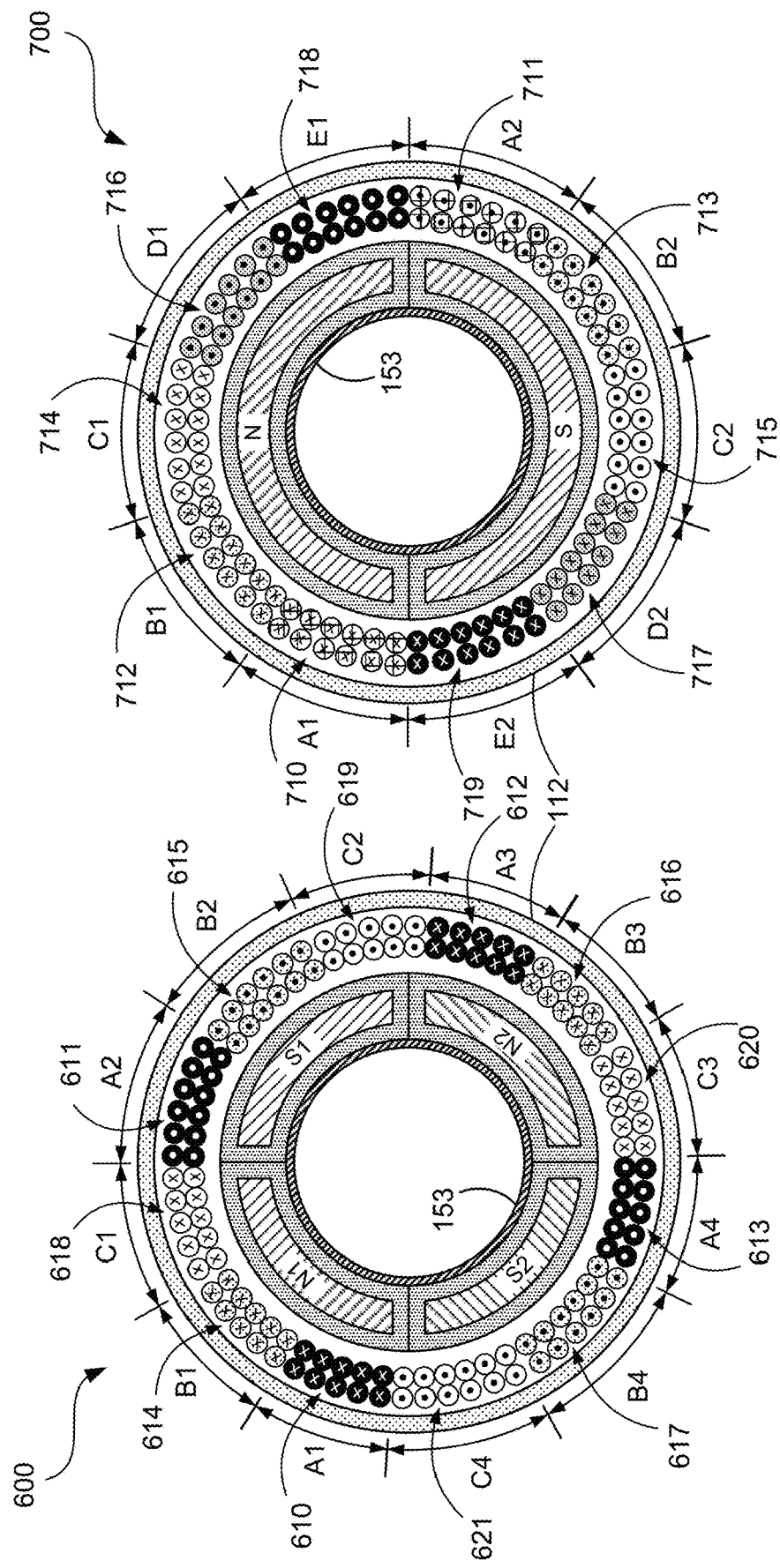

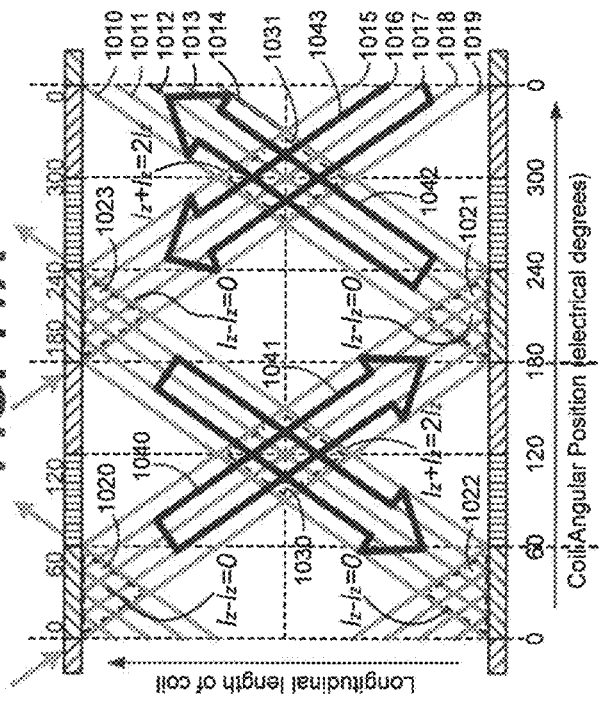
FIG. 11A
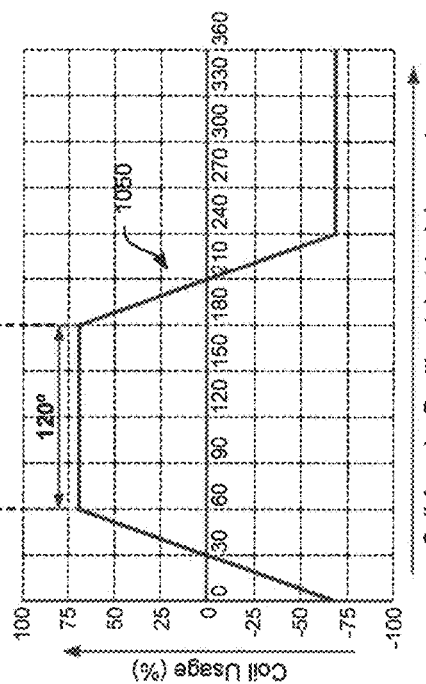
FIG. 11B
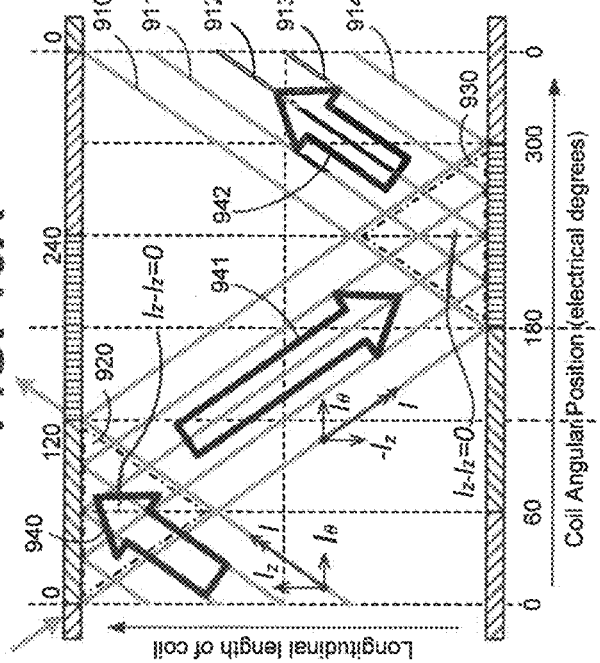
FIG. 10A
FIG. 10B

COIL WINDING PATTERN FOR ENHANCED MOTOR EFFICIENCY

CROSS REFERENCE TO RELATED APPLICATION

This application claims priority of U.S. Provisional Application No. 62/853,999 filed May 29, 2019, which is incorporated by reference herein.

BACKGROUND

Intravascular blood pumps such as the Impella® pump by Abiomed, Inc. of Danvers, MA, are quickly becoming the current standard for ventricular assist devices. The range of Impella® pumps currently comprises the Impella 2.5® pump, the Impella 5.0® pump, the Impella CP® pump and the Impella LD® pump. These pumps are inserted into a patient percutaneously through a single access point (e.g. radial access, femoral access, axillary access) such that the pump head can be placed into a desired location within the patient's body via small diameter (6-7 Fr) catheters. Such desired locations include, but are not limited to, the left or right ventricle of the patient's heart. The pump head comprises an electric motor that includes a stator winding configured to magnetically interact with a rotor for rotation thereof resulting in a volumetric flow of blood through the rotor and hence through the heart of the patient. Efficient motors that produce good flow rates are sought.

SUMMARY

Currently the Impella® pump is capable of delivering blood at flow rates between about 2.5 to about 5.0 liters per minute (lpm). However, with the use of Impella® in an increasing number of surgical procedures, a greater demand is being placed on the need to increase the blood flow rates produced beyond these levels. This means a higher rotor speed is required from the electric motor. However due to the small geometries involved, increasing the rotor speed has several implications that may affect the operation of such small sized pumps. For example, increasing the rotor speed may involve the increase in generation of heat (joule heating) within the electric motor. As the device is percutaneously inserted into the patient's body, any such increase in heat generation may have disastrous effects on surrounding tissue. Another consideration is the resistive load placed on the device where any modifications to the electrical motor to achieve a higher flow rate may lead to a decrease in motor efficiency due to resistive losses.

Given the shortcomings in the state of the art as identified above, there is significant need for increasing the flow rate produced by electric motors while maintaining or increasing the efficiency of the motor.

Disclosed herein are devices for addressing various problems and shortcomings of the state of the art, as identified above. More particularly, disclosed herein are intravascular blood pumps for insertion into a patient's body. Typically, the device will be positioned in the patient's vasculature such as, but not limited to, the patient's heart or aorta. In some aspects a portion of the device (e.g. a motor and rotor of the pump portion of the device) sits outside of the patient's heart (i.e. in the aorta) and another portion of the device (e.g. a cannula) extends into the patient's heart (e.g. the left ventricle). While certain aspects of the invention are described with the pump positioned in the heart, one of ordinary skill will appreciate that the pump may be positioned in other locations of the patient's vasculature. Any descriptions of the pump being positioned in the patient's heart are provided by way of illustration of one possible placement of the device in the patient's vasculature and not by way of limitation. The blood pump comprises an elongate housing having a proximal end connected to a catheter and a distal end connected to the pump, the housing having a longitudinal axis. The blood pump also comprises a slotless permanent magnet motor contained within the housing, the motor having p magnet pole pairs and n phases, where p is an integer greater than zero, and n is an integer $\geq 3$. The motor comprises a stator winding having 2np coils wound to form two coils per phase per magnet pole pair such that a coil from each phase is circumferentially arranged next to a coil from a different phase in a sequential order of phase, the arrangement repeated along the stator winding such that each coil of the 2np coils spans 360/(2np) mechanical degrees about the cross section of the stator winding. The motor also comprises a permanent magnet rotor supported for rotation and configured to generate a magnetic flux for interaction with the stator winding. The blood pump is configured such that the two coils per phase per magnet pole pair of the stator winding are connected in series such that a direction of current flow through a first coil of the two coils is opposite to a direction of current flow in a second coil of the two coils, the current flow in the first coil and the current flow in the second coil interacting with opposite polarities of the magnetic flux of the rotor for producing torque in the same direction, thereby facilitating rotation of the rotor for the flow of blood through the pump.

In another embodiment, there is provided a slotless permanent magnet electric motor having p magnet pole pairs and n phases, where p is an integer greater than zero, and n is an integer $\geq 3$, the motor having a longitudinal axis. The motor comprises a stator winding having 2np coils wound to form two coils per phase per magnet pole pair such that a coil from each phase is circumferentially arranged next to a coil from a different phase in a sequential order of phase, the arrangement repeated along the stator winding such that each coil of the 2np coils spans 360/(2np) mechanical degrees about the cross section of the stator winding. The motor also comprises a permanent magnet rotor supported for rotation and configured to generate a magnetic flux for interaction with the stator winding. The motor is configured such that the two coils per phase per magnet pole pair of the stator winding are connected in series such that a direction of current flow through a first coil of the two coils is opposite to a direction of current flow in a second coil of the two coils, the current flow in the first coil and the current flow in the second coil interacting with opposite polarities of the magnetic flux of the rotor for producing torque in the same direction, thereby facilitating rotation of the rotor.

In some implementations, each of the coils comprise either N/2 turns for even values of N, or (N±1)/2 for odd values of N, where N is the number of winding turns in a coil of a conventional stator winding having np coils wound to form one coil per phase per magnet pole pair, where N is an integer $\geq 1$. In certain implementations, the resistance of the two coils connected in series per phase is equivalent to the resistance of a single coil of the conventional stator winding. In other implementations, the two coils per phase are connected in series such that their start terminals or their end terminals are connected together.

In certain implementations, the two coils per phase are connected to the coils of the other phases in either a star or a delta configuration. In some implementations, the 2np coils comprise any one of helical windings, rhombic windings, conventional windings and hybrid windings. In other implementations, the stator winding has a coil usage function that defines a vertical component of the coil relative to the longitudinal length of the stator winding that interacts with the magnetic field of the rotor to contribute to the torque generated in the motor. In certain implementations, for helical coil windings, the coil usage function is maximized when the vertical component is two-thirds the longitudinal length of the stator winding. In some implementations, the coil usage function has the same form for all phases but shifted by 360/n electrical degrees for each phase.

In further implementations, the coil usage function defines a vertical component of a coil relative to the longitudinal length of the stator winding that contributes to a torque generated in the motor. In some implementations, the motor comprises a three-phase, two-pole machine. In other implementations, the motor comprises a six-coil two-pole machine, each coil spanning 60 mechanical degrees about the cross section of the stator winding. In certain implementations, the motor generates a torque constant that is about 15.5% greater than the torque constant of a motor having a conventional stator winding with np coils wound to form one coil per phase per magnet pole pair.

In other implementations, the rotor pumps blood at a rate between about 1.0 lpm and about 6.0 lpm. In some implementations, the pump may be inserted into the right ventricle of the patient's heart. In further implementation, the pump may be inserted into the left ventricle of the patient's heart.

The stator windings according to embodiments of the present disclosure employ two coils per phase per magnet pole pair, connected as described above. This provides for a 15.5% increase in torque constant in electric motors using such stator windings when compared to conventional electric motors having stator windings with one coil per phase per magnet pole pair. Such a stator configuration does not increase the resistive load on the stator, and thus reduces joule heating within the electric motor. In effect the electric motor of the present disclosure provides for a stator coil winding pattern with enhanced motor efficiency.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which:

FIG. 3A shows an illustrative cross section at the top end of a conventional stator winding as is known in the art that may be employed in the blood pump of FIG. 1;

FIG. 3B shows an illustrative cross section at the top end of a stator winding according to an embodiment of the present disclosure that may be employed in the blood pump of FIG. 1;

FIG. 6 shows an illustrative cross section of the stator winding for an electric motor having three phases and two pole pairs, for use in the blood pump of FIG. 1, according to an embodiment of the present disclosure;

FIG. 7 shows an illustrative cross section of the stator winding for an electric motor having five phases and one pole pair, for use in the blood pump of FIG. 1, according to an embodiment of the present disclosure;

FIG. 10A shows the current flow direction within the coils of one phase of the conventional stator winding in FIG. 3A at one instant during operation;

FIG. 10B shows the percentage of coil usage in one phase of the convention stator winding in FIG. 3A when used in the blood pump of FIG. 1;

FIG. 11A shows the current flow direction within the coils of one phase of the stator winding in FIG. 3B at one instant during operation, according to an embodiment of the present disclosure.

FIG. 11B shows the percentage of coil usage in one phase of the stator winding in FIG. 3B when used in the blood pump of FIG. 1, according to an embodiment of the present disclosure.

DETAILED DESCRIPTION

To provide an overall understanding of the devices described herein, certain illustrative embodiments will be described. Although the embodiments and features described herein are specifically described for use in connection with intravascular blood pumps, it will be understood that all the components and other features outlined below may be combined with one another in any suitable manner and may be adapted and applied to other types of procedures requiring an efficient electric motors with high rotor speeds.

The devices and methods described herein relate to an intravascular blood pump for insertion into a patient's body (i.e. the patient's vasculature such as the heart, aorta, etc.). The blood pump comprises an elongate housing having a proximal end connected to a catheter and a distal end connected to the pump, the housing having a longitudinal axis. The blood pump also comprises a slotless permanent magnet motor contained within the housing, the motor having p magnet pole pairs and n phases, where p is an integer greater than zero, and n is an integer ≥3. The motor comprises a stator winding having 2np coils wound to form two coils per phase per magnet pole pair such that a coil from each phase is circumferentially arranged next to a coil from a different phase in a sequential order of phase, the arrangement repeated along the stator winding such that each coil of the 2np coils spans 360/(2np) mechanical degrees about the cross section of the stator winding. The motor also comprises a permanent magnet rotor supported for rotation and configured to generate a magnetic flux for interaction with the stator winding. The blood pump is configured such that the two coils per phase per magnet pole pair of the stator winding are connected in series such that a direction of current flow through a first coil of the two coils is opposite to a direction of current flow in a second coil of the two coils, the current flow in the first coil and the current flow in the second coil interacting with opposite polarities of the magnetic flux of the rotor for producing torque in the same direction, thereby facilitating rotation of the rotor for the flow of blood through the pump.

The intravascular blood pump of the present disclosure allows for an increased motor efficiency by incorporating a double helical stator winding. Such a stator winding comprises two coils per phase per magnet pole pair connected in the abovementioned configuration. This provides for a 15.5% increase in torque constant over conventional blood pumps employing one coil per phase per magnet pole pair. Such a stator configuration does not increase the resistive load on the stator, and thus reduces joule heating within the electric motor. In effect the electric motor of the present disclosure provides for a stator coil winding pattern with enhanced motor efficiency.

Figure 1:
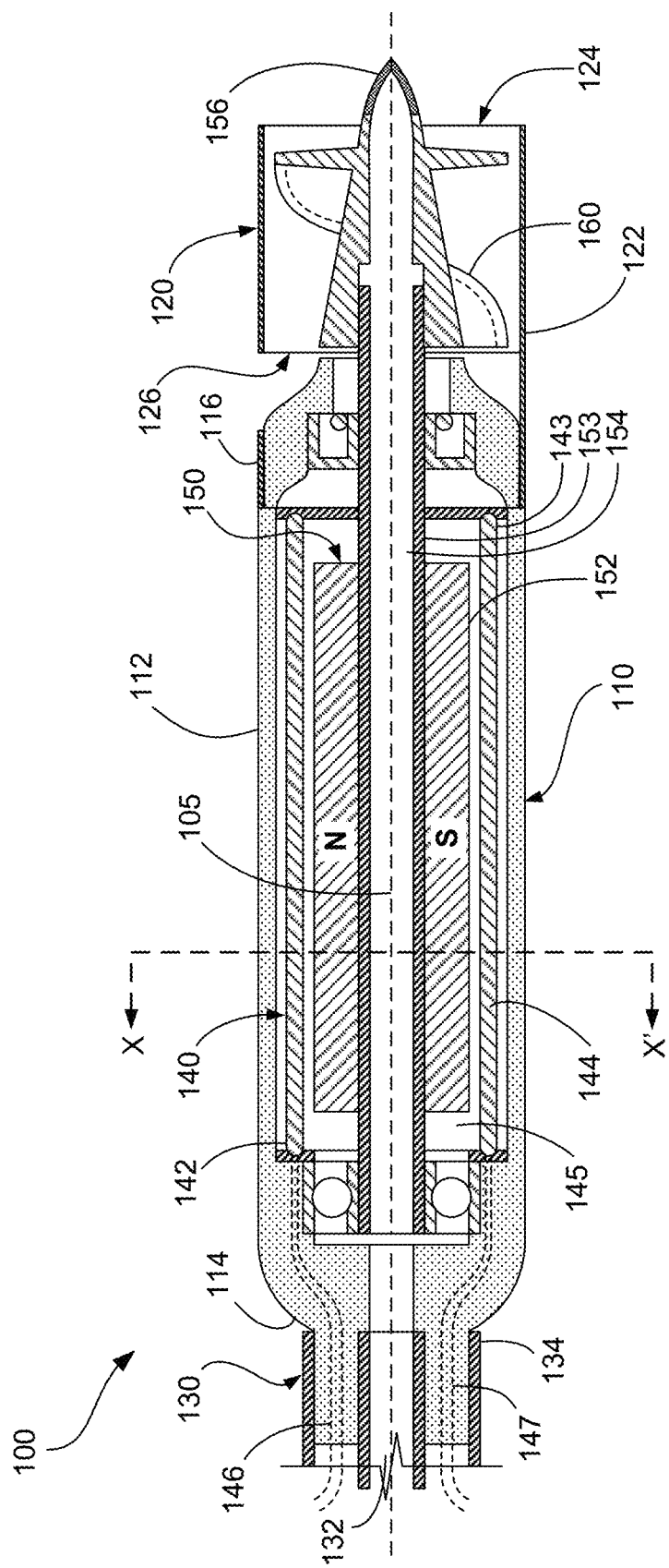
FIG. 1 shows an illustrative longitudinal cross section of an intravascular blood pump, according to an embodiment of the present disclosure.

FIG. 1 illustrates an exemplary intravascular blood pump 100 for insertion into the body of a patient, according to an embodiment of the present disclosure. Blood pump 100 comprises a motor unit 110 and a pump unit 120 arranged along a longitudinal axis 105. The motor unit 110 comprises an electric motor including a stator winding 140 and a rotor 150 contained within a housing 112. The stator winding 140 extends along the length of the motor unit 110 from a proximal end 142 to a distal end 143, and comprises wires 144 wound in a particular pattern, the details of which will be provided below. The stator winding 140 defines a central lumen 145 in which the rotor 150 is positioned. The stator winding 140 is slotless such that the wires 144 are wound upon themselves and not onto a conventional laminated stator core. Feed lines 146, 147 provide the necessary electrical connections externally from the pump 100 to the stator winding 140 for operation of the motor unit 110. Each of the wires 144 may have an insulating coating (not shown), and, optionally, the wound stator wires 144 may be encapsulated or over-molded by a synthetic epoxide resin (also not shown).

In FIG. 1, the stator winding 140 and the housing 112 are depicted as separate components, however it will be understood that the stator winding 140 may be encapsulated within the housing 112 to form a single component. The housing 112 comprises a proximal end 114 and a distal end 116. The proximal end 114 of the housing 112 is coupled to a distal end 134 of a catheter 130 which may comprise a flexible tube. Catheter 130 comprises a lumen 132 which extends towards the physician for control and operation of the blood pump 100.

The rotor 150 comprises a permanent magnet 152 that is rotationally supported about a shaft 153 within the lumen 145 of the stator 140. Magnet 152 may comprise a cylindrical permanent magnet that surrounds the shaft 153 within the motor unit 110. Shaft 153 extends from the motor unit 110 into the pump unit 120 and facilitates rotation of an impeller 160 for the pumping of blood. In certain implementations, the rotor 150 may comprise several permanent magnets radially arranged about the shaft 153, or an electromagnetic magnet having its own rotor windings. For example, for a motor having one pole pair, the magnet 152 may comprise one north pole N and one south pole S. As a further example, for a motor having two pole pairs, the magnet 152 may comprise two north poles N1 and N2, and two south poles, S1 and S2, arranged alternately around the shaft 153.

Further, while FIG. 1 illustrates the rotor 150 as rotatable within the stator 140, the electric motor 110 may be configured such that the stator 140 is held stationary about the shaft 153 and the rotor 150 is configured as a cylinder that rotates around the stator 140. Shaft 153 extends along the length of the motor unit 110 and extends into a cylindrical housing 122 of the pump unit 120. In some implementations, the shaft 153 may be hollow and comprise a lumen 154 for the passage of a guidewire, for example.

The distal end of the shaft 153 is coupled to an impeller 160 located within the pump housing 112. Interaction between the stator 140 and rotor 150 of the motor unit 110 generates torque in the rotor 150 causing the shaft 153 to rotate, which, in turn, causes the impeller 160 to rotate in the cylindrical pump housing 122. When this occurs, blood is sucked into the pump via an axial intake opening 124 for conveyance in the axial direction, the blood issuing laterally from the openings 126 and flowing axially along housing 112. In this manner the pump 100 generates a flow of blood within the heart of the patient.

FIGS. 2A-2D illustrate exemplary stator winding patterns 210-213 according to an embodiment of the present disclosure. In FIGS. 2A-2D the coil winding patterns for a single wire in a stator are shown, such as wires 142 in FIG. 1, however it will be understood that the complete stator winding, such as stator winding 140 in FIG. 1, will be obtained by the axial arrangement of a plurality of similarly wound wires about a longitudinal axis of the motor unit 110, such as the longitudinal axis 105 in FIG. 1.

Figure 2A:
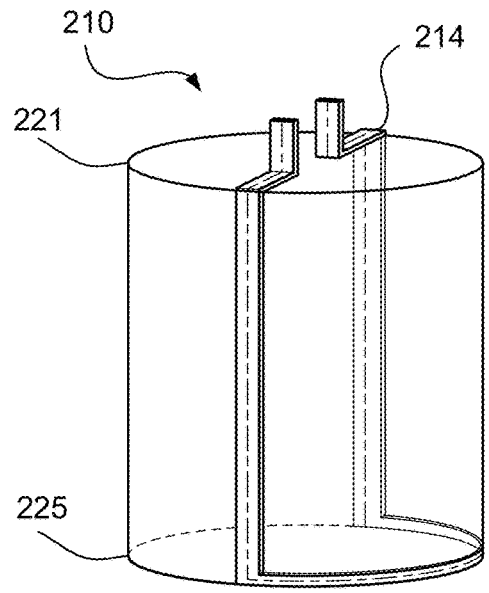
FIGS. 2A-2D show exemplary coil winding patterns as are known in the art that may be employed in the blood pump of FIG. 1.
Figure 2B:
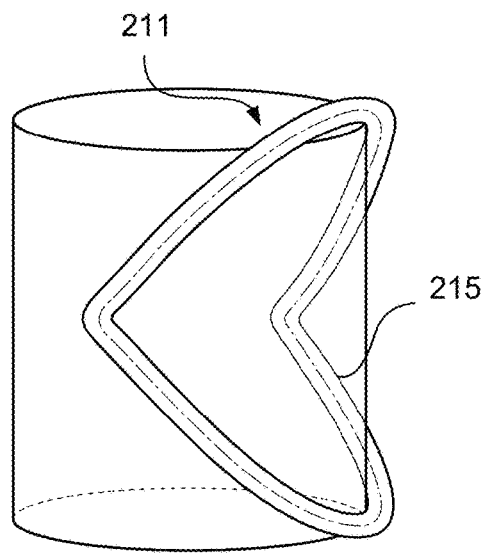

FIGS. 2A-2D illustrate exemplary coil winding patterns employed in two-pole electric machines in which one mechanical degree is equal to one electrical degree. The coil winding patterns in FIGS. 2A-2D may be used to form the stator winding 140 of the motor unit 110 in FIG. 1. FIG. 2A shows a conventional stator winding pattern 210 in which each wire 214 in the stator extends from a proximal end 221, along the length of the stator 220, to a distal end 225. At the distal end 225, the wire 214 follows the external perimeter of the stator for 180 mechanical degrees and returns to the proximal end 221. Because the end points of the wire 214 both end up at the proximal end 221, conventional coil winding patterns 210 may be faced with an end turn stack up issue in which each of the plurality of wire ends at the proximal end 221 of the stator winding 210 has to be electrically connected to the stator feed line, which, in turn, may cause crowding and connections issues. FIG. 2B shows a rhombic stator winding pattern 211 in which each wire 215 is arranged in a bent configuration. Unlike the conventional winding 210 in FIG. 2A, the rhombic winding comprises one continuous wire that is wound several times over, each complete turn shifted axially to form the stator coil. The bent configuration of the rhombic winding may require post-assembly.

Figure 2C:
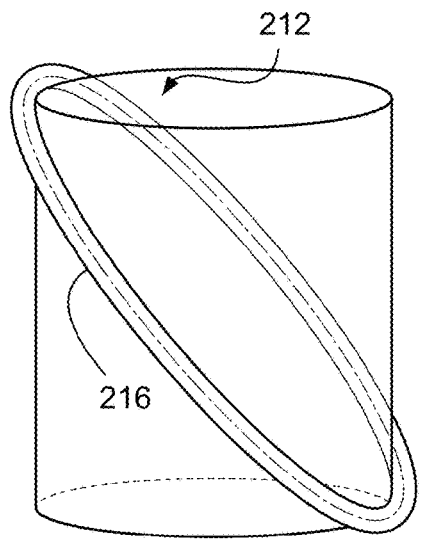
Figure 2D:
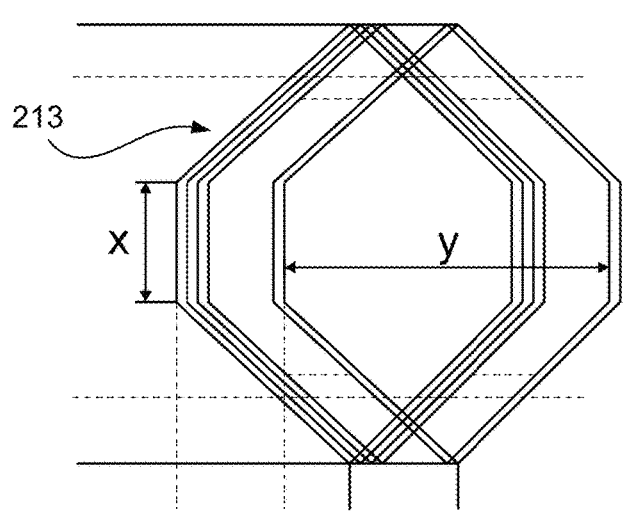

FIG. 2C shows a helical stator winding pattern 212 in which each wire 216 is arranged in an elliptical configuration around the stator. The helical stator winding pattern 212 is similar to the rhombic winding pattern 211 in FIG. 2B but without the bend which simplifies the coil winding process. The helical winding 212 is a one-step winding which can be easily formed without the need for any post-assembly steps. FIG. 2D shows a hybrid stator winding pattern 213 that comprises a winding that is a mixture of the conventional windings as shown in FIG. 2A and the rhombic windings as shown in FIG. 2B. Such a hybrid stator winding allows for the optimum ratio of torque to resistance by adjusting the vertical length, x, and/or horizontal angular span, y, of the coil.

The following disclosure makes use of the helical winding pattern 212 of FIG. 2B in the respective stator windings. However, it will be understood that the stator windings in the present disclosure may employ any of winding patterns as described in relation to FIGS. 2A-2D. Further, in some implementations of the present disclosure, any other stator winding patterns may be employed.

Embodiments of the present disclosure will be described with reference to a conventional stator winding having one coil per phase per permanent magnet pole pair. FIGS. 3A and 3B illustrate cross sections of exemplary stator windings for use in an electric motor, such as stator winding 140 of motor unit 110 in FIG. 1. FIG. 3A shows a conventional stator winding 300 comprising one coil per phase per permanent magnet pole pair for use in a three-phase electric motor having one pole pair (i.e. one north pole N and one south pole S). In the present disclosure, the three phases of the electric motor are referred to as phases A, B and C. In the conventional stator winding 300, each phase comprises one coil—coil 310 (labelled 'A') for phase A, coil 311 (labelled 'B') for phase B, and coil 312 (labeled 'C') for phase C. Each of the coils 310-312 comprises a winding having a plurality of N turns, where N is an integer and N>1, where each coil has the same number of turns. The windings are formed from wires that have been turned in a specific manner, such as that described in relation to FIGS. 2A-2D, thereby resulting in each coil having a start point and an end point, as indicated by the wire ends 320-325 in FIG. 3A. Embodiments of the present disclosure will be described with respect stator windings having helical coils; however, it will be understood that any winding type may be employed.

As seen in FIG. 3A, the lateral distribution of coils 310-312 is such that they are equally distributed about the stator winding 300 where each coil spans 120 electrical (equal to 120 mechanical degrees in a two-pole electrical machine) about the circumference of the cross section of the stator winding 300. While stator winding 300 is employed in a three-phase electric motor having one coil per magnet pole pair, for a general electric motor having n phases and p magnet pole pairs, each coil of a conventional stator winding 300 having one coil per phase per magnet pole pair would span 360/(np) mechanical degrees about the circumference of the cross section of the stator winding. As for the axial distribution of the coils about the longitudinal axis of the conventional stator winding 300, the windings of the coils 310-312 are configured such that they are each wound from the proximal end of the stator winding 300 (such as proximal end 142 of stator winding 140 in FIG. 1), extending longitudinally towards the distal end (such as distal end 143 of stator winding 140 in FIG. 1), and returning back to the proximal end. In this manner, each of the coils 310-312 of the stator winding 300 effectively comprises an inner layer and an outer layer, the outer layer overlaid on the inner layer, as shown in the cross section of FIG. 3A. In this configuration, the lead wires for each of the coils 310-312 are located at the proximal end of the stator winding 300 for connectivity with the feed lines to the electric motor, such as lead lines 146, 147 as shown in FIG. 1.

FIG. 3B shows a stator winding 350 comprising two coils per phase per magnet pole pair for use in a three-phase electric motor having one pole pair, according to an embodiment of the present disclosure. With this arrangement, stator winding 350 is a double coil winding, and, when implemented with helical coils as depicted in FIG. 2C, the stator winding 350 is a double helical coil winding. In the stator winding 350, each phase A, B and C of the three-phase electric motor comprises two coils. Thus, phase A comprises coil 360 (labelled 'A1') and coil 361 (labelled 'A2'), phase B comprises coil 362 (labelled 'B1') and coil 363 (labelled 'B2'), and phase C comprises coil 364 (labelled 'C1') and coil 365 (labelled 'C2'). With reference to the conventional stator winding 300 in FIG. 3A, if each coil 310-312 comprises a winding having N turns, where N is an integer and N≥1, each of the coils 360-365 of stator winding 350 comprises a winding having either N/2 turns for even values of N, or (N±1)/2 for odd values of N, with each coil having the same number of turns. Thus, each coil in the stator winding 350 comprises about half the number of turns as the coils in the conventional stator winding 300 in FIG. 3A. For example, if coils 310-312 of the conventional stator winding 300 comprises 100 turns each, coils 360-365 of the stator winding 350 would comprise about 50 turns each. The winding turns of each coil 360-365 may comprise any of the aforementioned winding types, such as, for example, a helical winding.

The lateral distribution of coils 360-365 is such that they are equally distributed about the stator winding 350 where each coil spans 60 mechanical degrees about the circumference of the cross section of the stator winding 350. While stator winding 350 is employed in a three-phase electric motor having two coils per phase per magnet pole pair, for a general electric motor having n phases and p magnet pole pairs, each coil of the stator winding 350 of the present disclosure having two coils per phase per magnet pole pair would span 360/(2np) mechanical degrees about the circumference of the cross section of the stator winding. The axial distribution of the coils in stator coil 350 is similar to that of the conventional stator coil 300. The axial distribution of the coils about the longitudinal axis of the stator winding 350 is such that the windings of the coils 360-365 are each wound from the proximal end of the stator winding 350 (such as proximal end 142 of stator winding 140 in FIG. 1), extending longitudinally towards the distal end (such as distal end 143 of stator winding 140 in FIG. 1), and returning back to the proximal end. In this manner, each of the coils 360-365 of the stator winding 350 effectively comprises an inner layer and an outer layer, the outer layer overlaid on the inner layer, as shown in the cross section of FIG. 3B. In this configuration, the lead wires for each of the coils 360-365 are located at the proximal end of the stator winding 300 for connectivity with the feed lines to the electric motor, such as lead lines 146, 147 as shown in FIG. 1.

Coils 310-312 in the conventional stator winding 300 and coils 360-365 of the stator winding 350 of the present disclosure may be electrically connected in any configuration for electric motors, such as, for example, a star connection or a delta connection. FIG. 4A shows the coils 310-312 of the stator winding 300 in FIG. 3A connected in an exemplary star configuration 400. Coils 310-312 are represented as their resistive loads RA, RB and RC, respectively. In the star configuration 400, the end point 'Ae' of coil 310, the end point 'Be' of coil 311, and the end point 'Ce' of coil 330, are connected together. The start point 'As' of coil 310, the start point 'Bs' of coil 311, and the start point 'Cs' of coil 312, are connected to a feed line, such as feed lines 143, 144 of the blood pump 100 in FIG. 1. In this manner, each branch of the star configuration 400 comprises a single load corresponding to the coils for each phase in the stator winding 300.

Figure 4B:
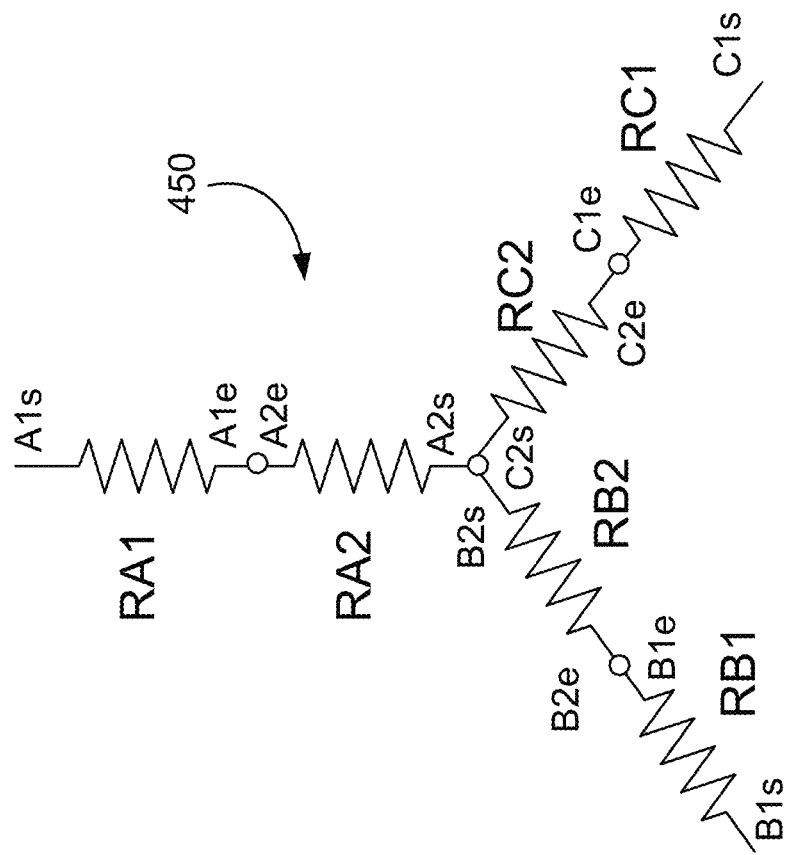
FIG. 4B shows an illustrative circuit schematic diagram illustrating the electrical connections of the coils comprising the stator winding of FIG. 3B when arranged in a star configuration, according to an embodiment of the present disclosure.
Figure 4A:
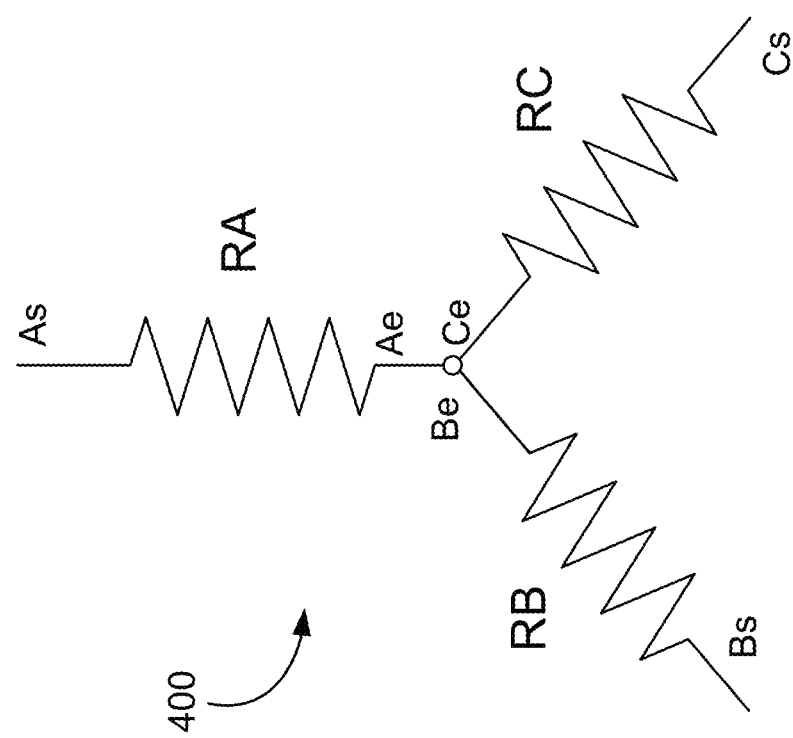
FIG. 4A shows an illustrative circuit schematic diagram illustrating the electrical connections of the coils comprising the stator winding of FIG. 3A when arranged in a star configuration.

FIG. 4B shows an exemplary electrical connection of the coils in the stator winding 350, according to an embodiment of the present disclosure. Here coils 360-361 are represented as resistive loads RA1 and RA2 for phase A, respectively, coils 362-363 are represented as resistive loads RB1 and RB2 for phase B, respectively, and coils 364-365 are represented as resistive loads RC1 and RC2 for phase C, respectively. As mentioned in the foregoing, coils 360-365 of stator winding 350 each comprise half the turns of coils 310-312 of stator winding 300. Thus, the resistive load per phase of the double stator winding 350 is the same as the resistive load per phase of the conventional stator winding 300, i.e. RA=RA1+RA2, RB=RB1+RB2, and RC=RC1+RC2. As such, the double coil configuration of stator winding 350 does not place an additional resistive load on the electric motor when compared to the load presented by conventional stator winding 300.

As shown in the connection diagram of FIG. 4B, each branch of the star configuration 450 comprises two coils having their like terminals connected, i.e. the two coils are connected back to back. For example, for phase A, coils 360-361 represented by resistive loads RA1 and RA2, respectively, are connected such that the end points 'A1$e$' and 'A2$e$' are connected together. Similarly, end points 'B1$e$' and 132$e'$ of coils 362-363 of phase B represented by resistive loads RB1 and RB2, respectively, are connected together, and end points 'C1$e$' and 'C2$e$' of coils 364-365 of phase C represented by resistive loads RC1 and RC2, respectively, are connected together. The start point 'A1$s$' of the resistive load RA1 of coil 360 for phase A, the start point 131$s'$ of the resistive load RB1 of coil 362 for phase B, and the start point 'C1$s$' of resistive load RC1 of coil 364 for phase C, are connected to a feed line, such as feed lined 143, 144 of the blood pump 100 in FIG. 1. Additionally, the start point 'A2$s$' of the resistive load RA2 of coil 361 for phase A, the start point 132$s'$ of the resistive load RB2 of coil 363 for phase B, and the start point 'C2$s$' of resistive load RC2 of coil 365 for phase C, are connected together.

The manner in which the coils 360-365 of the double stator winding 350 of the present disclosure are connected is important as it determines how the coils 360-365 interact with the magnetic flux generated by the rotor during operation of the electric motor. With the star configuration 450 as depicted in FIG. 4B, the direction of current flowing through coil A1 of stator winding 350 is opposite to the direction of current flowing through coil A2. Similarly, the direction of current flowing through coil B1 of stator winding 350 is opposite to the direction of current flowing through coil B2, and the direction of current flowing through coil C1 of stator winding 350 is opposite to the direction of current flowing through coil C2. This means that coil A1 having a first direction of current flowing therethrough interacts with a first pole of the rotor while coil A2 having a second direction of current flowing therethrough, opposite to the first direction of current in coil A1, interacts with a second pole of the rotor opposite the first pole. Additionally, coil B1 having a first direction of current flowing therethrough interacts with a first pole of the rotor while coil B2 having a second direction of current flowing therethrough, opposite to the first direction of current in coil B1, interacts with a second pole of the rotor opposite the first pole. Further, coil C1 having a first direction of current flowing therethrough interacts with a first pole of the rotor while coil C2 having a second direction of current flowing therethrough, opposite to the first direction of current in coil C1, interacts with a second pole of the rotor opposite the first pole. The interaction of the coils of the stator winding 350 with the magnetic flux of the rotor during operation will be described in relation to FIG. 5.

Figure 5:
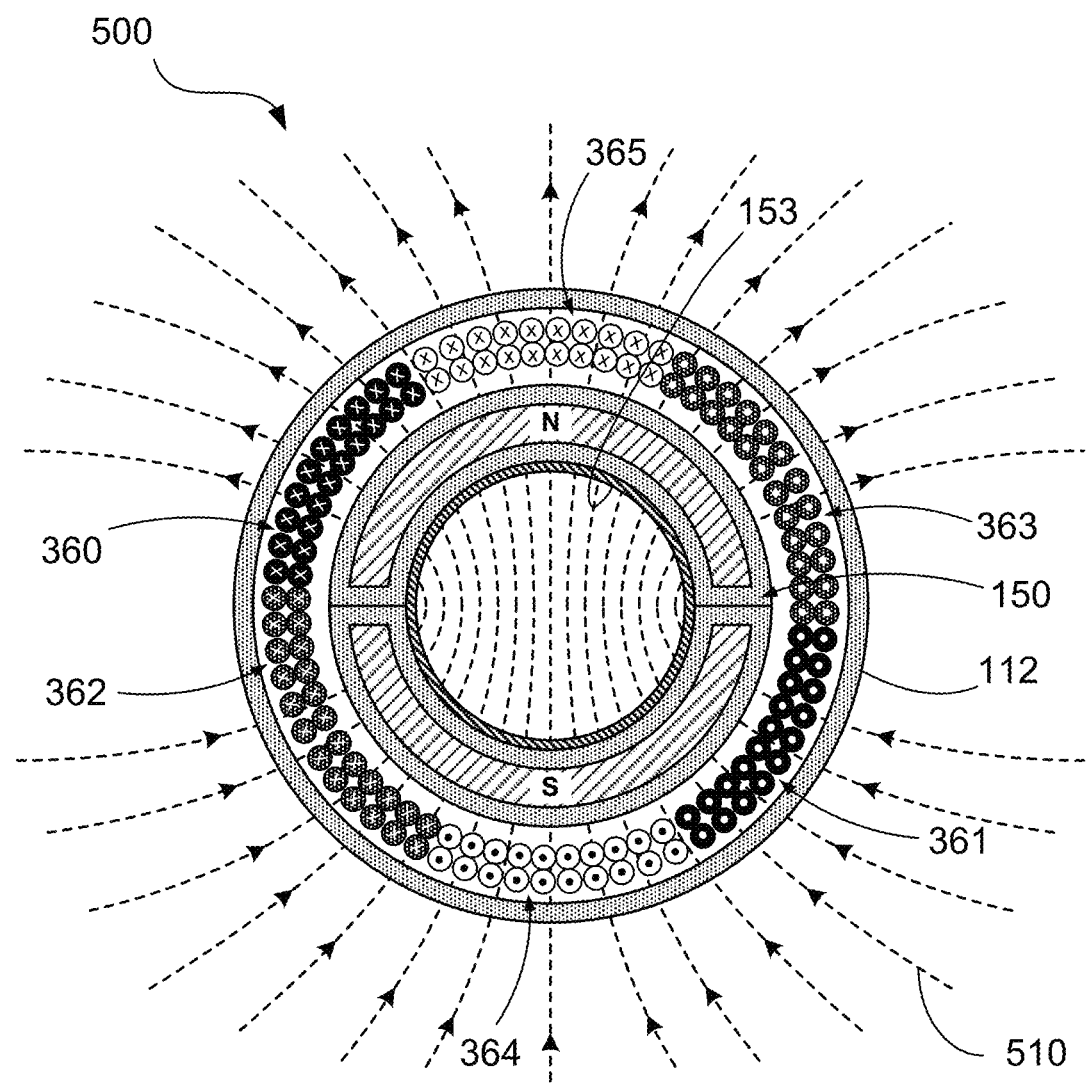
FIG. 5 shows an illustrative cross section of the stator winding of FIG. 3B during operation of the blood pump of FIG. 1, according to an embodiment of the present disclosure.

FIG. 5 illustrates an exemplary cross-section 500 of the blood pump 100 of FIG. 1 employing stator winding 350 in a three-phase two-pole electric motor, taken along line X-X' during operation. As previously mentioned, while stator winding 350 is suitable for the operation of a three-phase electric motor having two coils per phase per magnet pole pair, a stator winding for an electric motor having any number of phases n and magnet pole pairs p can be used within the scope of the present disclosure, bringing the total number of coils used to 2np. In FIG. 5, coils marked with an 'x' indicate current flowing into the page, orthogonal to the plane of the page, while coils marked with a '•' indicate current flowing out of the page, orthogonal to the plane of the page. As illustrated, coils 360-361 for phase A are connected as described in relation to FIG. 4B such that the direction of current flowing through coil 360 is opposite to the direction of current flowing through coil 361. With the physical arrangement and electrical connection of coils 360-361 as described in the foregoing, the polarity of the magnetic field generated from the permanent magnet stator 150 that coil 360 interacts with is opposite to that which interacts with coil 361.

Similarly, coils 362-363 for phase B of the electric motor are connected such that the direction of current flowing through coil 362 is opposite to the direction of current flowing through coil 363. With the physical arrangement and electrical connection of coils 362-363 as described in the foregoing, the polarity of the magnetic field generated from the permanent magnet stator 150 that coil 362 interacts with is opposite to that which interacts with coil 363. Further, coils 364-365 for phase C of the electric motor are connected such that the direction of current flowing through coil 362 is opposite to the direction of current flowing through coil 363. With this arrangement, coils 364-365 each see a different polarity from the magnet pole pair of the stator. With the physical arrangement and electrical connection of coils 364-365 as described in the foregoing, the polarity of the magnetic field generated from the permanent magnet stator 150 that coil 364 interacts with is opposite to that which interacts with coil 365. The interaction of the coils of the stator winding 350 with the magnetic flux of the rotor during operation generates a torque that acts on the rotor causing it to rotate.

FIG. 6 illustrates another example of a cross-section of a double coil stator winding 600 for use in an electric motor having three phases A, B and C, and two permanent magnet pole pairs N1-S1 and N2-S2, according to an embodiment of the present disclosure. According the aforementioned general definitions, the electric motor using stator winding 600 has n=3 and p=2. As discussed in relation to stator winding 350 in FIG. 4A, stator winding 600 also comprises two coils per phase per magnet pole pair resulting in 12 coils 610-621 in total. In the stator winding 600, due to the presence of two magnet pole pairs in the electric motor, each phase A, B and C of the three-phase electric motor comprises two coils. Thus, phase A comprises coils 610-613 (labelled 'A1,' 'A2,' 'A3' and 'A4' respectively), phase B comprises coils 614-617 (labelled 'B1,' 'B2,' 'B3' and 'B4' respectively), and phase C comprises coils 618-621 (labelled 'C1,' 'C2,' 'C3' and 'C4' respectively). As shown in FIG. 6, a coil from each phase is circumferentially arranged next to a coil from a different phase in a sequential order of phase, and that arrangement is repeated along the stator winding such that each coil spans 360°/(2np)=360°/(2×3×2)=30° about the cross-section of the stator winding 600.

As with the coils of stator winding 350, coils 610-621 may be electrically connected in either star or delta configuration in which (i) coils 610-613 for phase A are connected back to back with their like terminals together along the branch for phase A of the star or delta connection, (ii) coils 614-617 for phase B are connected back to back with their like terminals together along the branch for phase B of the star or delta connection, and (iii) coils 618-621 for phase C are connected back to back with their like terminals together along the branch for phase C of the star or delta connection. With such an electrical connection, (i) the direction of current flowing through coils A1 and A3 is opposite to the direction of current flowing through coils A2 and A4, (ii) the direction of current flowing through coils B1 and B3 is opposite to the direction of current flowing through coils B2 and B4, and (iii) the direction of current flowing through coils C1 and C3 is opposite to the direction of current flowing through coils C2 and C4.

In this manner, coil A1 having a first direction of current flowing therethrough interacts with a first pole N1 of the rotor, coil A2 having a second direction of current flowing therethrough, opposite to the first direction of current in coil A1, interacts with a second pole S1 of the rotor opposite the first pole N1, coil A3 having a first direction of current flowing therethrough interacts with a third pole N2 of the rotor, and coil A4 having a second direction of current flowing therethrough, opposite to the first direction of current in coil A3, interacts with a fourth pole S2 of the rotor opposite the third pole N2. Similarly, coil B1 having a first direction of current flowing therethrough interacts with a first pole N1 of the rotor, coil B2 having a second direction of current flowing therethrough, opposite to the first direction of current in coil B1, interacts with a second pole S1 of the rotor opposite the first pole N1, coil B3 having a first direction of current flowing therethrough interacts with a third pole N2 of the rotor, and coil B4 having a second direction of current flowing therethrough, opposite to the first direction of current in coil B3, interacts with a fourth pole S2 of the rotor opposite the third pole N2. Finally, coil C1 having a first direction of current flowing therethrough interacts with a first pole N1 of the rotor, coil C2 having a second direction of current flowing therethrough, opposite to the first direction of current in coil C1, interacts with a second pole S1 of the rotor opposite the first pole N1, coil C3 having a first direction of current flowing therethrough interacts with a third pole N2 of the rotor, and coil C4 having a second direction of current flowing therethrough, opposite to the first direction of current in coil C3, interacts with a fourth pole S2 of the rotor opposite the third pole N2. The interaction of the coils of the stator winding 600 with the magnetic flux of the rotor during operation generates a torque that acts on the rotor that causes the rotor to rotate.

FIG. 7 illustrates a further example of a cross-section of a double coil stator winding 700 for use in an electric motor having five phases A, B, C, D and E, and one permanent magnet pole pair N-S, according to an embodiment of the present disclosure. According the aforementioned general definitions, the electric motor using stator winding 700 has n=5 and p=1. As discussed in relation to stator windings 350 and 600, stator winding 700 also comprises two coils per phase per magnet pole pair resulting in 10 coils 710-719 in total. Phase A comprises coils 710-711 (labelled 'A1' and 'A2' respectively), phase B comprises coils 712-713 (labelled 'B1' and 132' respectively), phase C comprises coils 714-715 (labelled 'C1' and 'C2' respectively), phase D comprises coils 716-717 (labelled 'D1' and 'D2' respectively), and phase E comprises coils 718-719 (labelled 'E1' and 'E2' respectively). As shown in FIG. 7, a coil from each phase is circumferentially arranged next to a coil from a different phase in a sequential order of phase, and that arrangement is repeated along the stator winding 700 such that each coil spans 360°/(2np)=360°/(2×5×1)=36° about the cross-section of the stator winding 700.

As with the coils of stator windings 350 and 600, coils 710-719 may be electrically connected in either star or delta configuration in which (i) coils 710-711 for phase A are connected back to back with their like terminals together along the branch for phase A of the star or delta connection, (ii) coils 712-713 for phase B are connected back to back with their like terminals together along the branch for phase B of the star or delta connection, (iii) coils 714-715 for phase C are connected back to back with their like terminals together along the branch for phase C of the star or delta connection, (iv) coils 716-717 for phase D are connected back to back with their like terminals together along the branch for phase D of the star or delta connection, and (v) coils 718-719 for phase E are connected back to back with their like terminals together along the branch for phase E of the star or delta connection. With such an electrical connection, (i) the direction of current flowing through coil A1 is opposite to the direction of current flowing through coil A2, (ii) the direction of current flowing through coil B1 is opposite to the direction of current flowing through coil B2, (iii) the direction of current flowing through coil C1 is opposite to the direction of current flowing through coil C2, (iv) the direction of current flowing through coil D1 is opposite to the direction of current flowing through coil D2, and (v) the direction of current flowing through coil E1 is opposite to the direction of current flowing through coil E2.

In this manner, coil A1 having a first direction of current flowing therethrough interacts with a first pole N of the rotor, and coil A2 having a second direction of current flowing therethrough, opposite to the first direction of current in coil A1, interacts with a second pole S of the rotor opposite the first pole N. Similarly, coil B1 having a first direction of current flowing therethrough interacts with a first pole N of the rotor, and coil B2 having a second direction of current flowing therethrough, opposite to the first direction of current in coil B1, interacts with a second pole S of the rotor opposite the first pole N. Further, coil C1 having a first direction of current flowing therethrough interacts with a first pole N of the rotor, and coil C2 having a second direction of current flowing therethrough, opposite to the first direction of current in coil C1, interacts with a second pole S of the rotor opposite the first pole N. Coil D1 having a first direction of current flowing therethrough interacts with a first pole N of the rotor, and coil D2 having a second direction of current flowing therethrough, opposite to the first direction of current in coil D1, interacts with a second pole S of the rotor opposite the first pole N. Finally, coil E1 having a first direction of current flowing therethrough interacts with a first pole N of the rotor, and coil E2 having a second direction of current flowing therethrough, opposite to the first direction of current in coil E1, interacts with a second pole S of the rotor opposite the first pole N. The interaction of the coils of the stator winding 700 with the magnetic flux of the rotor during operation generates a torque that acts on the rotor that causes the rotor to rotate.

The interaction of the current flowing in the coils of the stator winding 350 with the magnetic flux density of the two-pole rotor during operation will be described by referring back to FIG. 5. As described in relation to FIG. 1, rotor 150 is in constant rotation when in use. FIG. 5 depicts the position of the rotor 150 at an instant when the rotor is radially positioned as shown, and with the direction of current flowing through the coils of the stator winding 350 as indicated. In the illustrated position, the permanent magnet rotor 150 produces a magnetic flux density B that is represented by a magnetic field pattern comprising magnetic field lines 510. The magnetic field lines 510 begin at the north pole N and end at the south pole S of the rotor 150. According to Lenz's law the interaction between the magnetic flux density B and the length of the stator winding L in a direction perpendicular to the magnetic flux density B generates a torque T within the rotor 150 for rotation thereof, governed by the equation:

$$T \propto (B\hat{r} \times L\hat{z}) \quad (1)$$

where $\hat{z}$ is a direction parallel to the longitudinal axis 105 of the rotor 150, $B\hat{r}$ is a radial component of the magnetic flux density, that is perpendicular to the longitudinal axis 105 of the rotor 150, $L\hat{z}$ is the vertical component of coil winding that is parallel to the longitudinal access of the motor rotor and × denotes the vector cross product. Thus, the flow of current in stator winding 350 causes rotation of the rotor 150 about the longitudinal axis 105, which, in turn, causes a corresponding rotation of the impeller 160 coupled to the distal end of the rotor shaft 153.

Figure 8A:
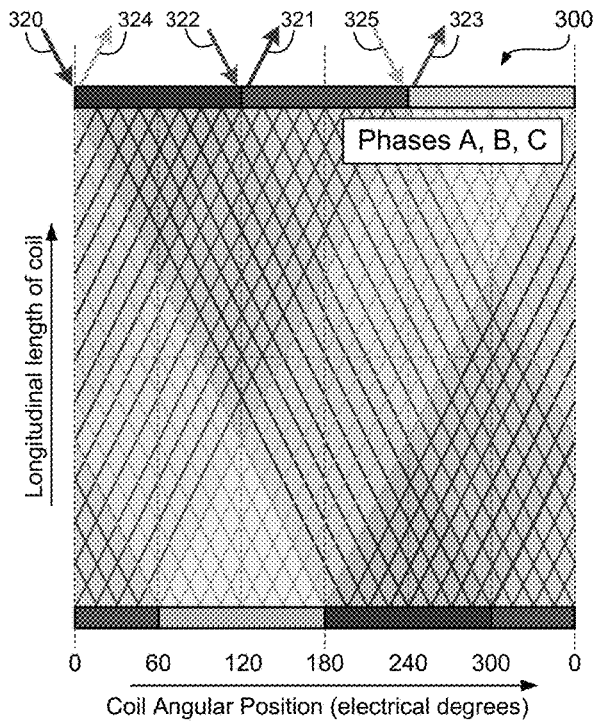
FIGS. 8A-8D show the coil winding pattern for the conventional helical winding of FIG. 3A.
Figure 8B:
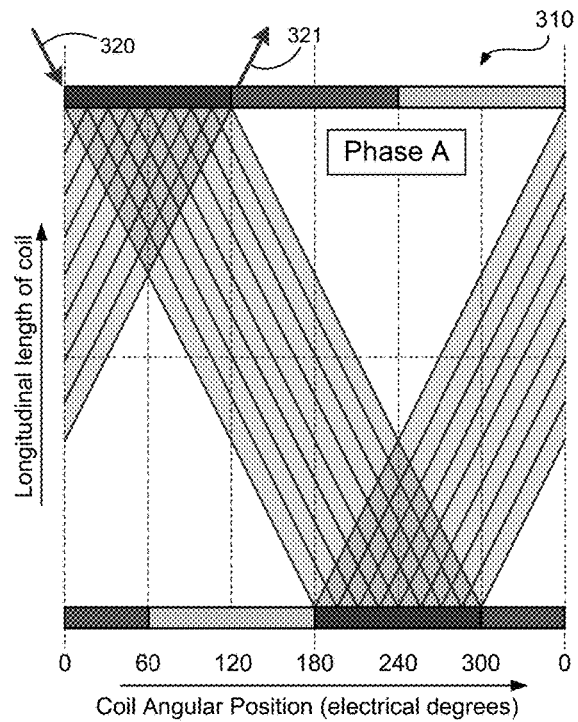
Figure 8C:
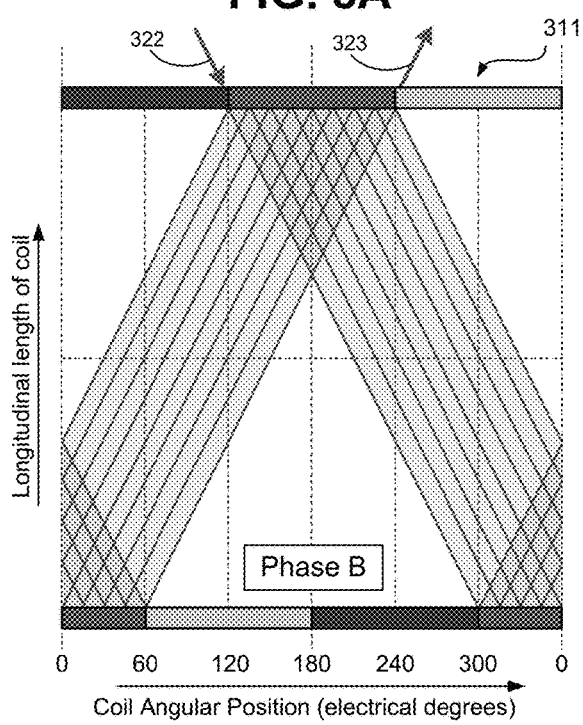
Figure 8D:
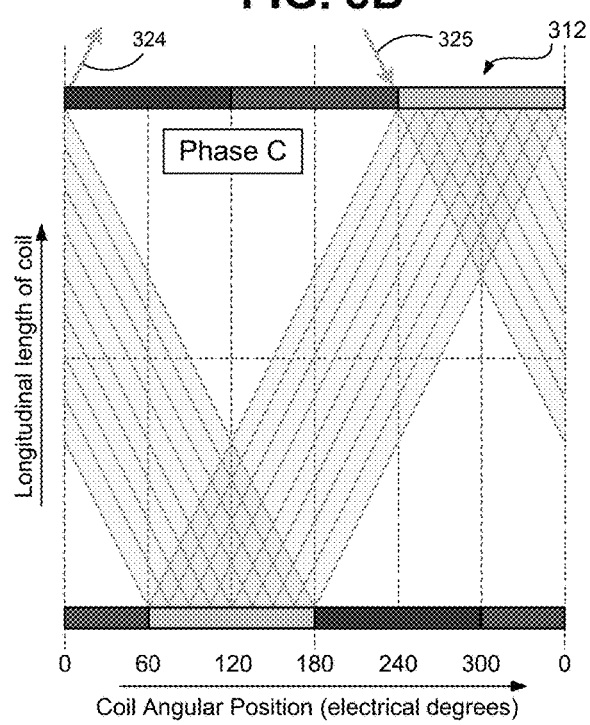

FIG. 8A illustrates the conventional stator winding 300 during use in a three-phase two-pole electric motor in which one electrical degree equals to one mechanical degree. The horizontal axis of the plot represents the angular position along the circumference of the stator winding 300 and the vertical axis represents the longitudinal length of the stator winding 300 moving from the distal end to the proximal end of the stator winding 300. As previously mentioned, each of coils 310-312 comprises a plurality of wires wound in a particular manner, such as, for example the helical winding of FIG. 2C. In FIG. 8A, the wires are wound helically and each of the coils 310-312 is shown as a band that is arranged between the proximal end (top end of the plot) and the distal end (bottom end of the plot) of the stator winding 300. Due to the manner in which the helical coils 310-312 are wound, each of bands in FIG. 8A overlap to form the stator winding 300. For improved visualization, FIGS. 8B-8D illustrate each of the winding patterns of coils 310-312 for phases A, B and C in stator winding 300 when viewed separately— when the coils as shown in FIGS. 8B-8D are overlaid, the stator winding 300 as shown in FIG. 8A results. Additionally, it should be noted that while each band representing coils 310-312 comprises a plurality of wires, only nine representative wires are shown per coil in FIGS. 8A-8D. Wire ends or lead lines 320-325 for each of the coils 310-312 are also shown at the proximal end of the stator winding 300. The direction shown on each lead line 320-325 represents the direction of winding the wires forming the respective coils 310-312. For example, the direction indicated on lead line 320 represents the starting point of the wire forming winding 310 and lead line 321 indicates the end point of the wire forming winding 310. Coils 310-312 are arranged in the stator winding 300 in an angular symmetric manner such that a coil from each phase is circumferentially arranged next to a coil from a different phase in a sequentially order of phase, thus resulting in the stator winding pattern as shown in FIG. 8A. The coil span for each of the coils 310-312 of stator winding 300 is 360°/(np)=360°/(3×1)=120°.

During operation of the electric motor, electrical current from a motor controller, is passed through the stator winding 300 via the feed lines, such as feed lines 146-147 in FIG. 1, connected to the wire ends 320-325 such that the magnitude of current flowing through each of the coils 310-312 is the same. As the coils 310-312 overlap in their arrangement within the stator winding 300, the effect of current flow in each of the coils may be influenced by the current flow in an adjacent or overlapping coil. Thus, due to the physical arrangement of the coils 310-312 in the stator winding, the net effect of the current flow through all the coils 310-312 of stator winding 300 cancel out. This effect will be further discussed in relation to FIG. 10A.

FIG. 10A illustrates only coil 310 (coil A) of the stator winding 300 during use. Coil A corresponds to phase A. Coil 310 is shown comprising only five representative winding wires 910-914, however it will be understood that coil 310 comprises a plurality of wires that form a band (as shown in FIG. 8A). As can be seen, the path taken by the current in each of the winding wires 910-914 have regions of overlap as the wires are wound between the proximal and distal ends of the stator winding 300 (such as proximal end 142 and distal end 143 as shown in FIG. 1). For example, due to the winding direction of the wires 910-914 in the coil 310, the current in the wires 910-914 flows into the triangular region 920, and then turn and leave the triangular region 920. When the wires 910-914 turn and leave the triangular region 920, the longitudinal component of current in the wires changes. This is shown in FIG. 10A, where the current I flowing in wire 914 entering triangular regions 920 has directional components $I_z$ and $I_\theta$ (longitudinal and angular components, respectively). When leaving triangular region 920, the current I changes direction and has directional components $-I_z$ and $I_\theta$. Thus, longitudinal component of current $-I_z$ leaving triangular region 920 is opposite to the longitudinal component of current $I_z$ entering triangular region 920. Similarly, the current in the wires 910-914 flow into the triangular region 930, and then turn and leave the region 930. When the wires 910-914 turn and leave the triangular region 930, the longitudinal component of current in the wires changes and is completely opposite to the longitudinal component of current in the wires entering triangular region 930. Because the magnitudes of the currents in wires 910-914 are the same and the longitudinal component of current flow are in complete opposition to each other entering and leaving the triangular regions 920 and 930, the effect of the longitudinal component of currents in wires 910-914 (represented by arrows 940-942 in FIG. 10A) on the rotor cancel out in triangular regions 920 and 930, i.e. $I_z - I_z = 0$ as indicated in FIG. 10A. Thus, the longitudinal component of current in the wires 910-914 in triangular regions 920 and 930 does not contribute to the torque developed in the rotor, per equation (1).

As described in equation (1), the torque T generated within the rotor 150 is dependent on the longitudinal length L of the current carrying wires of the coil in a direction parallel to the longitudinal axis 105 of the rotor 150. Thus, only the vertical directional component of wires 910-914 in FIG. 10A contributes to the generated torque T within the rotor. The vertical component of the wires 910-914 can be easily visualized by drawing a vertical line in FIG. 10A and determining the direction of the longitudinal component current flowing in the wires 910-914 at the point of intersection of the wires 910-914 and the vertical line.

The contribution of the mechanical arrangement of the wires in the coil to the generated torque T is described by a coil usage function 950, as shown in FIG. 10B. The vertical component of the wires 910-914 that contributes to the torque Tin the rotor can be seen in FIG. 10A where wires 910-914 carrying current with longitudinal components in opposing directions do not overlap. For example, for coil angular positions θ of 120° to 180° about the stator winding 300, there is no overlap of wires and the currents flowing in wires 910-914 have a longitudinal component that is in the same direction, however at the coil angular position θ of 60° and 240° about the stator winding 300, respectively, the wires overlap and the longitudinal component of current flowing in the overlapped wires 910-914 is in completely opposing directions.

Accordingly, the coil usage function is at its maximum when the longitudinal component of current flowing in wires 910-914 is in the same direction, as can be seen in FIG. 10B for 120°≤θ≤180° and 300°≤θ≤360° about the stator winding 300, where there are no overlapping wires carrying currents having longitudinal components that are in opposing directions. This maximum is about ⅔ the full length of the stator winding 300 for a three-phase two-pole electric motor, as shown in FIG. 10B where the coil usage is maximum at about 66.7%. The coil usage function is zero at θ=60° and θ=240° about the stator winding 300 where the wires overlap and the longitudinal component of current in the overlapped wires is equal but opposite in direction. For completeness, for 0°<θ<60°, 60°<θ<120°, 180°<θ<240°, and 240°<θ<300°, the wires 910-915 are partly overlapped with currents having longitudinal components in opposing directions, resulting in some contribution towards the torque T generated in the rotor. This can be seen in FIG. 9B where the coil usage varies linearly with θ for 0°<θ<60°, 60°<θ<120°, 180°<θ<240°, and 240°<θ<300°.

Figure 9A:
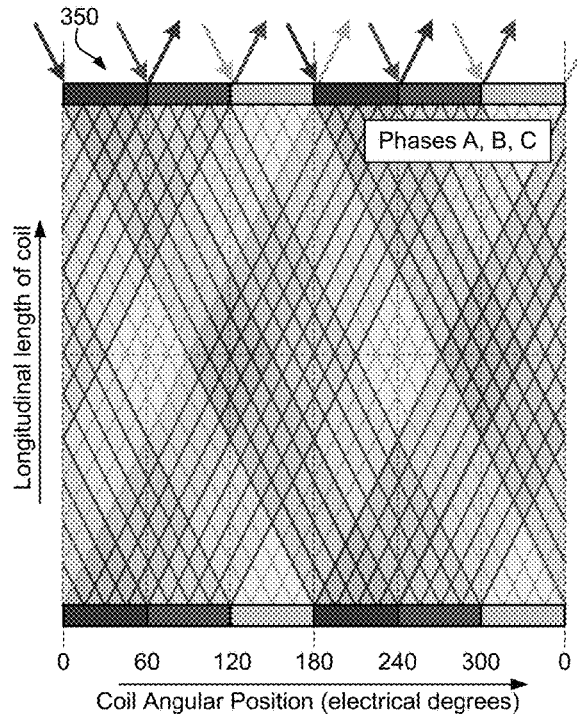
FIGS. 9A-9D show the coil winding pattern for the coils of the helical winding of FIG. 3B, according to an embodiment of the present disclosure.
Figure 9B:
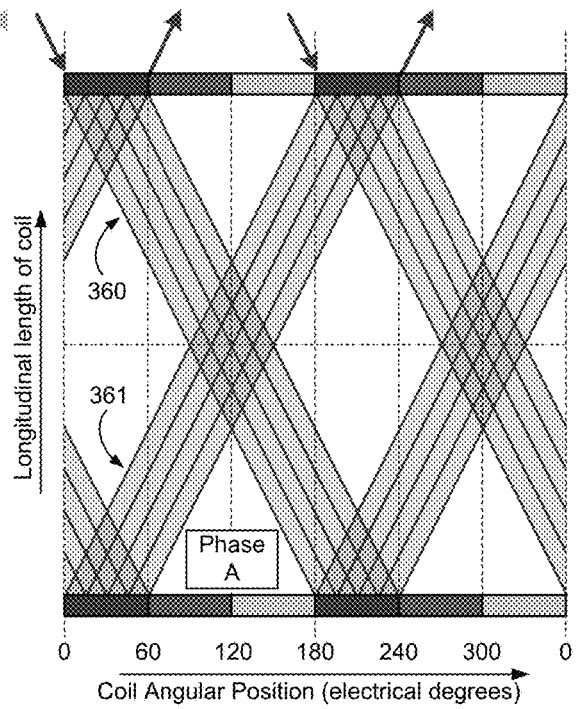
Figure 9C:
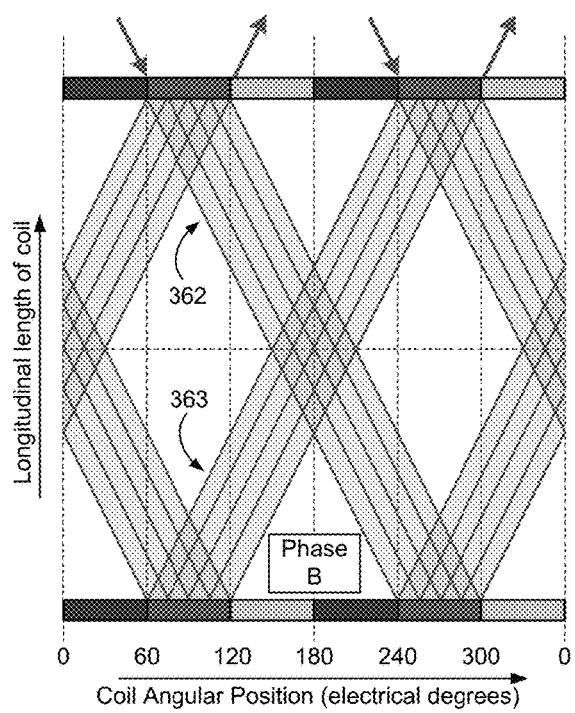
Figure 9D:
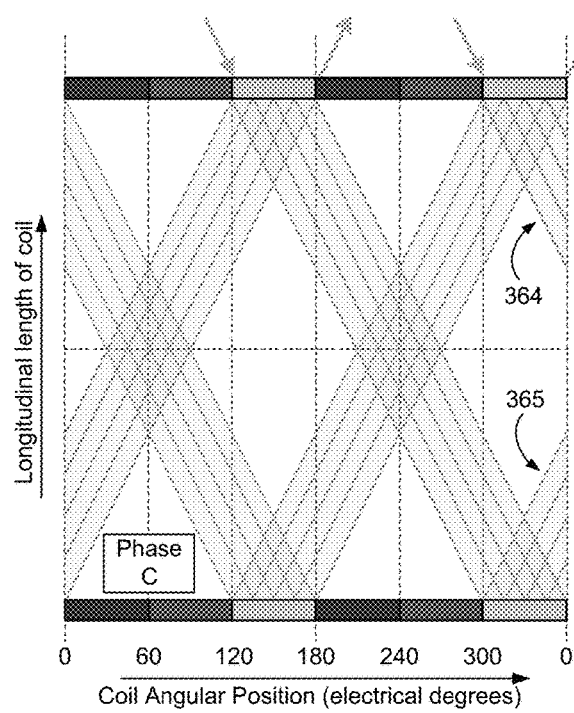

FIG. 9A illustrates the stator winding 350 according to an embodiment of the present disclosure during use in a three-phase two-pole electric motor at one instant during operation. As described in the foregoing, coils 360-365 are wound using helical windings, such as the helical winding 212 of FIG. 2C, however any winding type may be used. In FIG. 9A, the coils 360-365 are shown as bands that are arranged between the proximal end (top end of the plot) and the distal end (bottom end of the plot) of the stator winding 350. Due to the manner in which the helical coils 360-365 are wound, each of bands in FIG. 9A overlap to form the stator winding 350. As with FIGS. 8B-8D, for improved visualization, FIGS. 9B-9D illustrate each of the winding patterns of coils 360-365 for phases A, B and C in stator winding 350 when viewed separately—when the coils as shown in FIGS. 9B-9D are overlaid, the stator winding 350 as shown in FIG. 9A results. Additionally, it should be noted that while each band representing coils 360-365 comprises a plurality of wires, only five representative wires are shown per coil in FIGS. 9A-9D. Wire ends or lead lines for each of the coils 360-365 are also shown at the proximal end of the stator winding 350, with arrows indicating the direction of winding of wires forming the respective coils 360-365.

Coils 360-365 are arranged in the stator winding 350 in an angular symmetric manner such that a coil from each phase A, B and C is circumferentially arranged next to a coil from a different phase in a sequential order of phase, thus resulting in the stator winding pattern as shown in FIG. 9A. As previously described, the present disclosure relates to a stator winding having two coils per phase per magnet pole pair. Thus in FIGS. 9A-9D, phase A is shown as comprising coils 360-361 in FIG. 9B, phase B is shown as comprising coils 362-363 in FIG. 9C, and phase C is shown as comprising coils 364-365 The coils span for each of the coils 360-365 of stator winding 350 is 360°/(2np)=360°/(2×3×1)=60°.

During operation of the electric motor, direct current from a six-step direct current controller (not shown) is passed through the stator winding 350 via feed lines, such as feed lines 146-147 in FIG. 1, connected to the lead lines at the proximal end of the stator winding 350 such that the magnitude of current flowing through each of the coils 360-365 is the same. As the coils 360-365 overlap in their arrangement within the stator winding 350, the effect of current flow in each of the coils may be influenced by the current flow in an adjacent or overlapping coil. Unlike the conventional stator winding 300 shown in FIG. 8A, due to the physical arrangement of the coils in stator winding 350, the effect of the current flow through the coils 360-365 does not cancel out.

FIG. 11A illustrates only coils 360-361 (coils A1 and A2) of the stator winding 350 according to an embodiment of the present disclosure, during use. Coils A1 and A2 correspond to phase A. Coils 360 is shown comprising five representative winding wires 1010-1014 and coil 361 is shown comprising five representative winding wires 1015-1019, however it will be understood that each of coils 360-361 comprise a plurality of wires that form a band (as shown in FIG. 9A). As can be seen, the path taken by the current in each of the winding wires 1010-1019 have regions of overlap as the wires are wound between the proximal and distal ends of the stator winding 350 (such as proximal end 142 and distal end 143 as shown in FIG. 1). For example, the current in the wires 1010-1014 flow into triangular regions 1020 and 1021, and then turn and leave the triangular regions 1020-1021. Similarly, the current in the wires 1015-1019 flow into the triangular regions 1022-1023, and then turn and leave the triangular regions 1022-1023.

As described in relation to FIG. 10A, when the wires 1010-1014 turn and leave the triangular regions 1020-1021, and when wires 1015-1019 turn and leave the triangular regions 1022-1023, the longitudinal component of current in the respective wires changes. In wires 1010-1014, (i) the longitudinal component of current flowing out of triangular region 1020 is opposite to the longitudinal component of current flowing into the triangle region 1020, and (ii) the longitudinal component of current flowing out of triangular region 1021 is opposite to the longitudinal component of current flowing into the triangle region 1021. When the wires 1010-1014 turn and leave the triangular regions 1020-1021, the longitudinal component of current in the wires changes and is completely opposite to the longitudinal component of current flow in the wires entering triangular regions 1020-1021.

Similarly, in wires 1015-1019, (iii) the longitudinal component of current flowing out of triangular region 1022 is opposite to the longitudinal component of current flowing into the triangle region 1022, and (iv) the longitudinal component of current flowing out of triangular region 1023 is opposite to the longitudinal component of current flowing into the triangle region 1023. When the wires 1015-1019 turn and leave the triangular regions 1022-1023, the longitudinal component of current in the wires changes and is completely opposite to the longitudinal component of current in the wires entering triangular regions 1022-1023. Because the magnitudes of the currents in wires 1010-1019 are the same and the longitudinal component of current flow are in complete opposition to each other entering and leaving the triangular regions 1020-1023, the effect of the currents in wires 1010-1019 (represented by arrows 1040-

1043 in FIG. 11A) cancel out in regions 1020-1023, i.e. $I_z-I_z=0$ as indicated in FIG. 11A.

However, as the stator winding 350 has two coils per phase per magnet pole pair, i.e. a double winding, coils 360-361 also comprise additional diamond shaped regions of overlap 1030-1031. As shown in FIG. 11A, these diamond shaped regions of overlap occur away from the proximal or distal ends of the coils 360-361. In effect, these diamond shaped regions are actually back to back triangular regions that result when bands from coils A1 and A2 overlap with each other. In these diamond shaped regions, the longitudinal component of current in the wires 1010-1019 flows into the regions 1030-1031 in one direction, and then leave the regions 1030-1031 in the same direction. Because the magnitudes of the currents in wires 1010-1019 are the same and the longitudinal component of current flow are the same to each other in regions 1030-1031, the effect of the currents in wires 1010-1019 represented by arrows 1040-1043 in FIG. 11A, do not cancel out, but add together in regions 1030-1031, i.e. $I_z+I_z=2I_z$ as indicated in FIG. 11A. These diamond shaped regions of overlap 1030-1031 in which the effects of the longitudinal component of current flowing through wires 1010-1019 do not cancel increases the coil usage for phase A. These regions 1030-1031 are effectively positive zones which enhance the performance of the stator coil 350. While FIG. 11A describes the effect of current flow in coils 360-361 for phase A of stator winding 350, a similar effect will be seen from current flow in coils 362-365 for phases B and C of stator winding 350.

It should be noted that in the stator winding 350 according to embodiments of the present disclosure, the regions 1020-1023 are effectively dead zones in which the effect of the currents flowing through the windings cancel out. These dead zones are much smaller compared to regions 920 and 930 of the conventional stator winding 300. At the same time, due to the manner in which stator winding 350 is formed, additional positive zones are formed which improves the performance of the stator winding 350.

As described in relation to equation (1), the torque T generated within the rotor 150 is dependent on the longitudinal length L of the current carrying wires of the coil in a direction parallel to the longitudinal axis 105 of the rotor 150. In effect, only the vertical directional component of wires 1010-1019 in FIG. 11A contributes to the generated torque T within the rotor. The vertical component of the wires 1010-1019 can be easily visualized by drawing a vertical line on FIG. 11A and determining the direction of current flowing in the wires 1010-1019 that intersect with the vertical line.

The contribution of the mechanical arrangement of the wires in the coil 350 to the generated torque T is described by a coil usage function 1050, as shown in FIG. 11B. The vertical component of the wires 1010-1019 that contributes to the torque T in the rotor 150 can be seen in FIG. 11A where wires 1010-1019 carrying current with longitudinal components in opposing directions do not overlap. For example, for $60°\leq\theta\leq180°$ about the stator winding 350, the current flowing in wires 1010-1019 have longitudinal components that are in the same direction (despite the wires overlapping in regions 1030 and 1031), however at the coil angular position θ of 30° and 210° about the stator winding 350, respectively, the wires overlap and the longitudinal component of current flowing in the overlapped wires 1010-1019 is in completely opposing directions.

Accordingly, the coil usage function is at its maximum when the longitudinal component of current flowing in wires 1010-1019 is in the same direction, as can be seen in FIG. 11B for $60°\leq\theta\leq180°$ and $240°\leq\theta\leq360°$ about the stator winding 350, where there are no overlapping wires carrying currents with longitudinal components in opposing directions. As with stator winding 300, this maximum is about ⅔ the full length of the stator winding 350 for a three-phase two-pole electric motor, as shown in FIG. 11B where the coil usage is maximum at about 66.7%. It should be noted that the maximum coil usage for stator winding 350 (for the coil angular range (120°)) is twice that for stator winding 300 (for the coil angular range (60°)). The coil usage function is zero at θ=30° and θ=210° about the stator winding 350 where the wires overlap and the longitudinal component of current flow in the overlapped wires is equal but in complete opposite in directions. For completeness, for $0°<\theta<30°$, $30°<\theta<60°$, $180°<\theta<210°$, and $210°<\theta<240°$, the wires 1010-1019 are partly overlapped, resulting in some contribution towards the torque T generated in the rotor. This can be seen in FIG. 11B where the coil usage varies linearly with θ for $0°<\theta<30°$, $30°<\theta<60°$, $180°<\theta<210°$, and $210°<\theta<240°$.

Figure 12A:
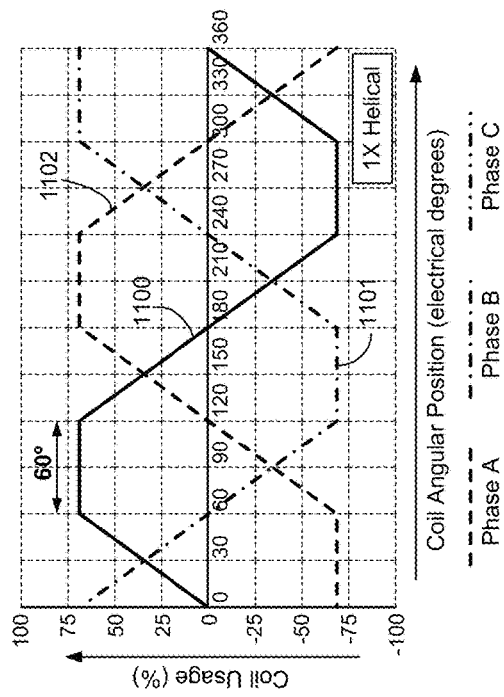
FIG. 12A-12D illustrates the increase in torque constant of a motor of a blood pump employing the stator winding of FIG. 3B, according to an embodiment of the present disclosure.
Figure 12B:
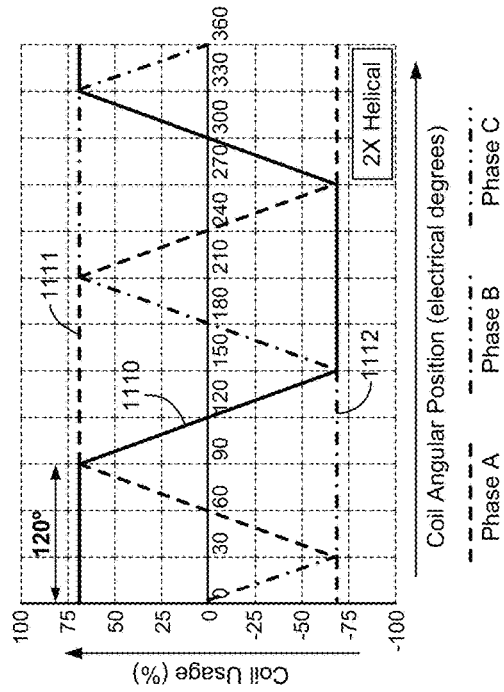
Figure 12C:
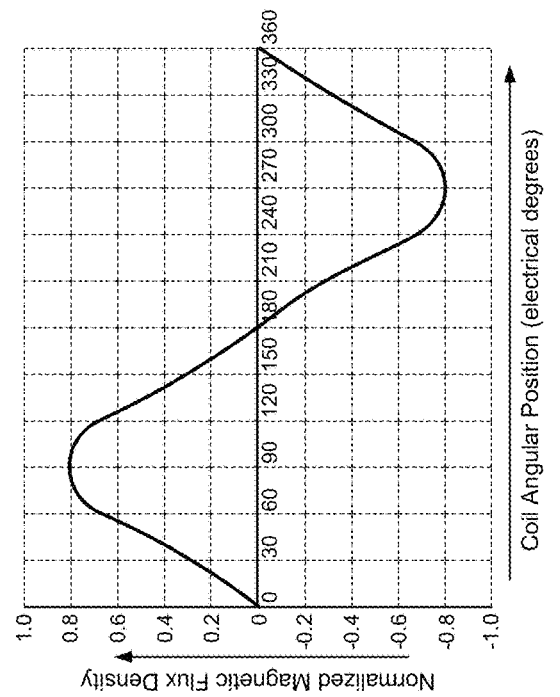

FIG. 12A illustrates the coil usage functions 1100-1102 for all three phases A, B and C, respectively, for the conventional stator winding 300. The usage function for each phase in FIG. 12A is identical to that shown in FIG. 10B. FIG. 12B illustrates the coil usage functions 1110-1112 for all three phases A, B and C, respectively, for the stator winding 350 according to an embodiment of the present disclosure. The usage function for each phase in FIG. 12B is identical to that shown in FIG. 11B. The usage functions shown in FIGS. 12A-12B are similar in shape for all three phases, and the curves for each phase are shifted by 120° from the previous phase. FIG. 12C illustrates the variation in magnetic flux density B about the angular position of the stator winding for the electric motor having one magnetic pole pair, at an instant in time. As the magnetic rotor of the electric motor rotates in time, the magnetic flux density curve of FIG. 12C would be of the same shape but would move along the horizontal axis as the north and south poles rotate about the longitudinal axis 105 of the rotor 150.

From FIGS. 12A-12C, and using Lenz's law (equation (1)), the torque T generated in the conventional stator winding 300 and the stator winding 350 of the present disclosure can be determined by using the relation:

$$T \propto \int B\hat{r} \times dL\hat{z}, \qquad (2)$$

which is essentially the area under the magnetic flux density curve in FIG. 12C multiplied by the respective coil usage functions in FIGS. 12A-12B. By definition, the torque constant $k_T$ is the torque T per unit current I, and thus the torque constant can be determined using the relation:

$$K_T \propto \int B\hat{r} \times dL\hat{z} \qquad (3)$$

Figure 12D:
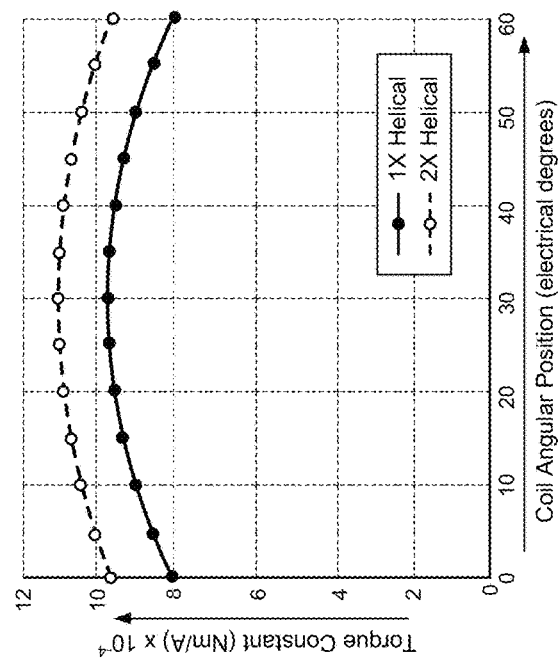

FIG. 12D shows the resulting torque constant $K_T$ generated in the conventional stator winding 300 (labelled as '1× Helical') and the stator winding 350 according to embodiments of the present disclosure (labelled as '2× Helical') for one complete torque cycle. Using a six-step direct current motor controller, one complete torque cycle spans 60°. As can be seen in FIG. 12D, the torque constant for the double coil stator winding 350 is increased by about 15.5% from that of the conventional stator winding 300 for one torque cycle of the electric motor. By 'about' what is meant is that this value is susceptible to variation by about 20%, i.e. the increase in torque brought about by the double helical stator winding 350 of the present disclosure may be in the range of 12.4% to 18.6%. This definition of 'about' applies to any other recitation in the present disclosure. In some implementations of the present disclosure, the increase in torque may be at least about 15.5%.

Table 1 shows representative data for two blood pumps having three-phase two-pole electric motors with single helical and double helical stator windings. Specifically, the single helical stator winding is similar to the conventional stator winding 300 as described in the foregoing, implemented with the helical winding type 212 as shown in FIG. 2C. The double helical stator winding is similar to the stator winding 350 as described in the foregoing, also implemented with the helical winding type. As can be seen, the double helical stator winding results in an electric motor with the same coil resistance of 5.25Ω/phase as that of the conventional single helical winding, and with an increased torque constant of $1.182\times10^{-3}$ N·m/A, i.e. an increase of 15.5% from that of the conventional single helical winding. Noticeably, the average current in the coils of the double helical stator winding has decreased by about 13.3%, thus indicating that the heating within the coils of the double helical stator winding has also decreased (as the coils resistance has not changed). The results in Table 1 confirm that the double helical stator winding according to embodiments of the present disclosure improves the efficiency of electric motors and hence blood pumps employing such stator windings. The blood pumps employing the above described stator windings comprising two coils per phase per permanent magnet pole pair are configured to operate at a flow rate of about 1.0 lpm and about 6.0 lpm, where 'lpm' indicates liters per minute.

TABLE 1

Performance of blood pumps with various stator coil configurations.

| Stator coil type | Single helical | Double helical |
| --- | --- | --- |
| Torque constant (N · m/A) × $10^{-3}$ | 1.023 | 1.182 |
| Coil Resistance per phase (Ω) | 5.25 | 5.25 |
| Average current (A) × $10^{-3}$ | 919 | 796 |

The foregoing is merely illustrative of the principles of the disclosure, and the devices and methods can be practiced by other than the described implementations, which are presented for purposes of illustration and not of limitation. It is to be understood that the devices described herein, while shown in respect of a double helical stator winding of an electric motor for a blood pump, may be applied to other systems in which an electric motor with increased torque and high motor efficiency is desired.

In the foregoing disclosure, it will be understood that the term 'about' should be taken to mean±20% of the stated value. Further, the term electric motor should be taken to be synonymous with the term electric machine, as is widely known in the art. All measure of degrees (with unit °) should be taken as mechanical degrees unless otherwise stated.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

The invention claimed is:

1. An intravascular blood pump for insertion into a patient's body, the pump comprising:
an elongate housing having a proximal end connected to a catheter and a distal end connected to the pump, the housing having a longitudinal axis; and
a slotless permanent magnet motor contained within the housing, the motor having p magnet pole pairs and n phases, where p is an integer greater than one, and n is an integer ≥3, the motor comprising:
a stator winding having 2np coils wound to form two coils per phase per magnet pole pair such that a coil from each phase is circumferentially arranged next to a coil from a different phase in a sequential order of phase, the arrangement repeated along the stator winding such that each coil of the 2np coils spans 360/(2np) mechanical degrees about a cross section of the stator winding each coil having an inner layer and an outer layer, the outer layer overlaid on the inner layer, and
a permanent magnet rotor supported for rotation and configured to generate a magnetic flux for interaction with the stator winding,
wherein the two coils per phase per magnet pole pair of the stator winding are connected in series such that a direction of current flow through a first coil of the two coils is opposite to a direction of current flow in a second coil of the two coils, the current flow in the first coil and the current flow in the second coil interacting with opposite polarities of the magnetic flux of the rotor for producing torque in the same direction, thereby facilitating rotation of the rotor for a flow of blood through the pump.

2. The intravascular blood pump of claim 1, wherein each of the coils comprise either N/2 winding turns or (N±1)/2 winding turns, where N is a number of winding turns in a coil of a conventional stator winding having np coils wound to form one coil per phase per magnet pole pair, where N is an integer ≥1.

3. The intravascular blood pump of claim 1, wherein the two coils per phase are connected in series such that their start terminals or their end terminals are connected together.

4. The intravascular blood pump of claim 1, wherein the two coils per phase are connected to the coils of the other phases in either a star or a delta configuration.

5. The intravascular blood pump of claim 1, wherein the 2np coils comprise any one of helical windings, rhombic windings, conventional windings and hybrid windings.

6. The intravascular blood pump of claim 1, wherein the stator winding has a coil usage function that defines a vertical component of the coil relative to a longitudinal length of the stator winding that interacts with a magnetic field of the rotor to contribute to the torque generated in the motor, the coil usage function maximized when the vertical component is two-thirds the longitudinal length of the stator winding.

7. The intravascular blood pump of claim 6, the coil usage function has the same form for all phases and is shifted by 360/n electrical degrees for each phase.

8. The intravascular blood pump of claim 7, wherein the coil usage function defines a vertical component of a coil relative to the longitudinal length of the stator winding that contributes to a torque generated in the motor.

9. The intravascular blood pump of claim 1, wherein the motor comprises a three-phase two-pole machine.

10. The intravascular blood pump of claim 1, wherein the motor comprises a six-coil two-pole machine, each coil spanning 60 mechanical degrees about the cross section of the stator winding.

11. The intravascular blood pump of claim 9, wherein the motor generates a torque constant that is about 15.5% greater than the torque generated by a motor having a stator winding with np coils wound to form one coil per phase per magnet pole pair.

12. The intravascular blood pump of claim 1, wherein the rotor pumps blood at a rate between about 1.0 lpm and about 6.0 lpm.

13. A slotless permanent magnet electric motor having p magnet pole pairs and n phases, where p is an integer greater than one, and n is an integer ≥3, the motor having a longitudinal axis and comprising:
   a stator winding having 2np coils wound to form two coils per phase per magnet pole pair such that a coil from each phase is circumferentially arranged next to a coil from a different phase in a sequential order of phase, the arrangement repeated along the stator winding such that each coil of the 2np coils spans 360/(2np) mechanical degrees about a cross section of the stator winding each coil having an inner layer and an outer layer, the outer layer overlaid on the inner layer, and
   a permanent magnet rotor supported for rotation and configured to generate a magnetic flux for interaction with the stator winding,
   wherein the two coils per phase per magnet pole pair of the stator winding are connected in series such that a direction of current flow through a first coil of the two coils is opposite to a direction of current flow in a second coil of the two coils, the current flow in the first coil and the current flow in the second coil interacting with opposite polarities of the magnetic flux of the rotor for producing torque in the same direction, thereby facilitating rotation of the rotor.

14. The slotless permanent magnet electric motor of claim 13, wherein each of the coils comprise either N/2 winding turns for even values or (N±1)/2 winding turns for odd values of N, where N is a number of winding turns in a coil of a conventional stator winding having np coils wound to form one coil per phase per magnet pole pair, where N is an integer ≥1.

15. The slotless permanent magnet electric motor of claim 14, wherein the resistance of the two coils connected in series per phase is equivalent to the resistance of a single coil of a stator winding.

16. The slotless permanent magnet electric motor of claim 13, wherein the two coils per phase are connected in series such that their start terminals or their end terminals are connected together.

17. The slotless permanent magnet electric motor of claim 13, wherein the two coils per phase are connected to the coils of the other phases in either a star or a delta configuration.

18. The slotless permanent magnet electric motor of claim 13, wherein the 2np coils comprise any one of helical windings, rhombic windings, conventional windings and hybrid windings.

19. The slotless permanent magnet electric motor of claim 13, wherein the stator winding has a coil usage function that defines a vertical component of the coil relative to a longitudinal length of the stator winding that interacts with a magnetic field of the rotor to contribute to the torque generated in the motor, the coil usage function maximized when the vertical component is two-thirds the longitudinal length of the stator winding.

20. The slotless permanent magnet electric motor of claim 19, wherein the coil usage function has the same form for all phases but shifted by 360/n electrical degrees for each phase.

21. The slotless permanent magnet electric motor of claim 13, wherein a coil usage function defines a vertical component of a coil relative to the longitudinal length of the stator winding that contributes to a torque generated in the motor.

22. The slotless permanent magnet electric motor of claim 13, wherein the motor comprises a three-phase two-pole machine.

23. The slotless permanent magnet electric motor of claim 13, wherein the motor comprises a six-coil two-pole machine, each coil spanning 60 mechanical degrees about the cross section of the stator winding.

24. The slotless permanent magnet electric motor of claim 22, wherein the motor generates a torque constant that is about 15.5% greater than the torque generated by a motor having a conventional stator winding with np coils wound to form one coil per phase per magnet pole pair.

* * * * *